(12) United States Patent
Kawaoka et al.

(10) Patent No.: US 8,507,247 B2
(45) Date of Patent: Aug. 13, 2013

(54) INFLUENZA A VIRUS WITH ATTENUATING MUTATIONS IN NS2 PROTEIN

(75) Inventors: Yoshihiro Kawaoka, Middleton, WI (US); Hatice Akarsu, Cambridge (GB); Kiyoko Iwatsuki-Horimoto, Tokyo (JP)

(73) Assignee: Wisconsin Alumni Research Foundation, Madison, WI (US)

( * ) Notice: Subject to any disclaimer, the term of this patent is extended or adjusted under 35 U.S.C. 154(b) by 168 days.

(21) Appl. No.: 12/854,578

(22) Filed: Aug. 11, 2010

(65) Prior Publication Data

US 2011/0081373 A1    Apr. 7, 2011

Related U.S. Application Data

(60) Provisional application No. 61/273,956, filed on Aug. 11, 2009.

(51) Int. Cl.
*C12N 7/00*    (2006.01)

(52) U.S. Cl.
USPC ........................................ 435/235.1; 435/236

(58) Field of Classification Search
None
See application file for complete search history.

(56) References Cited

PUBLICATIONS

Treanor et al (Virology 171:1-9, 1989).*
Karsu et al (EMBO Journal 22:4646-4655, 2003).*
Lee et al (Avian Diseases 50:561-571, 2006).*
Genbank ABD36884.1 (2007).*
Genbank CY002484.1 (2005).*

* cited by examiner

*Primary Examiner* — Mary E Mosher
(74) *Attorney, Agent, or Firm* — Schwegman Lundberg & Woessner, P.A.

(57) ABSTRACT

The invention provides an isolated attenuated recombinant influenza virus comprising a gene segment comprising a mutant NS2 protein gene, wherein the NS2 protein has at least two substitutions that do not substantially alter the in vitro replication of the virus but are associated with attenuation of the virus in vivo, wherein at least one of the substitutions is a substitution for glutamate.

15 Claims, 12 Drawing Sheets

Figure 2:
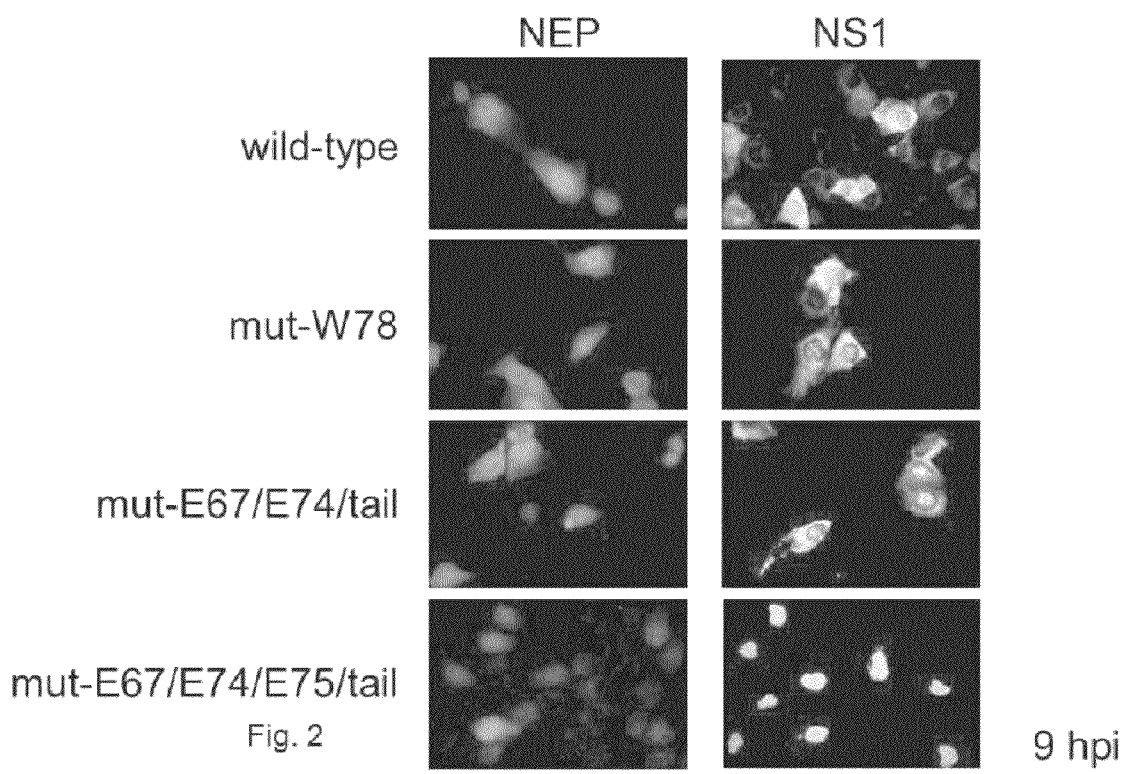

|  | NEP M1-binding domain | | | | NS1 C-terminal | |
|---|---|---|---|---|---|---|
|  | 67 | 74,75 | 78 | 82 | 217 | 230 |
| WSN | EQLGQKFEEIRWLIEE | | | | KQKRKMAGTIRSEV | |
| mut-W78 | EQLGQKFEEIRSLIEE | | | | KQKRKMAGTIRSEV | |
| mut-E75 | EQLGQKFESIRWLIEE | | | | KQKRKMAGTIRSEV | |
| mut-E67/E74/tail | SQLGQKFSEIRWLIEE | | | | KQKRKMAVAIRSEVFGNKMVD | |
| mut-E67/E74/E75/tail | SQLGQKFSSIRWLIEE | | | | KQKRKMAVAIRSEVFVDKMVD | |
| Udorn | EQLGQKFEEIRWLIEE | | | | KQKRKMARTARSKVRRDKMAD | 237 |
| B/Lee/40 | ETIRLATEELYLLSKR | | | | | |

"tail"

*FIG. 1*

FIG. 5

NS2
B
  1 madnmtttqi ewrmkkmaig ssthsssvlm kdiqsqfeql klrwesypnl vkstdyhqkr
 61 etirlateel yllskridds ilfhktvian ssiiadmivs lslletlyem kdvvevysrq
121 cl (SEQ ID NO: 1)

B
  1 madnmtttqi ewrmkkmaig ssthsssvlm kdiqsqfeql klrwesypnl vkstdyhqkr
 61 etirlvteel yllskriddn ilfhktvian ssiiadmivs lslletlyem kdvvevysrq
121 cl (SEQ ID NO: 2)

A H7N3
  1 mdsntvssfq dilmrmskmq lgsssedlng mitqfeslkl yrdslgeavm rmgdlhslqn
 61 rngkwreqls qkfeeirwli eevrhrlkvt ensfeqitfm qalqllleve qeirtfsfql
121 i (SEQ ID NO: 3)

H9N2
  1 mdsntvssfq diltrmskmq lgsssedlng mitqfeslkl yrdslgeavm rmgdlhslqn
 61 rngkwreqls qkfeeirwli eevrhrlrit ensfeqitfm qalqllleve qeirtfsfql
121 i (SEQ ID NO: 4)

H3N2
  1 mdsntvssfq dillrmskmq lgsssedlng mitqfeslki yrdslgeavm rmgdlhllqn
 61 rngkwreqlg qkfeeirwli eevrhrlkti ensfeqitfm qalqllfeve qeirtfsfql
121 i (SEQ ID NO: 5)

H5N1
  1 mdsntvssfq dilkrmskmq lgsssedlng mitqfeslkl yrdslgeavm rmgdlhslqn
 61 rngkwreqls qkfeeirwli eevrhrlrit ensfeqitfm qalqllleve qeirtfsfql
121 i (SEQ ID NO: 6)

C
  1 msdktvkstn lmafvatkml erqedldtct emqvekmkts tkarlrtess faprtwedai
 61 kdeilrrsvd tssldrwpel kqelenvsda lkadslwlpm kslslysevs nqepssipig
121 emkhqiltrl klicsrlekl dhnlskavlg iqnsedlili iynrdvcknt ilmikslcns
181 li (SEQ ID NO: 7)

NS1
B
  1 madnmtttqi evgpgatnat infeagilec yerlswqral dypgqdrlnr lkrklesrik
 61 thnksepesk rmsleerkai gvkmmkvllf mdpsagiegf epycmksssn sncpkynwtd
121 ypstpgrcld dieeepedvd gpteivlrdm nnkdarqkik eevntqkegk trltikrdir
181 nvlslrvlvn gtflkhpngy kslstlhrln aydqsgriva klvatddltv edeedghril
241 nslferlneg hpkpiraaet avgvlsqfgq ehrlspeegd n (SEQ ID NO: 8)

*FIG. 8A*

A H7N3
  1 mdsntvssfq vdcflwhvrk rfadqelgda pfldrlrrdq kslrgrgstl gldietatra
 61 gkqiverile eesdealkmt iasvpasryl tdmtleemsr dwfmlmpkqk vagslcirmd
121 qaimnkniil kanfsvifdr letlillraf teegaiigei splpslpght dedvknaigv
181 ligglewndn tvrvsetlqr fawrssnedg rpplppkqkr kmartiesev (SEQ ID NO: 9)

A H9N2
  1 mdsntvssfq vdcflwhvrk rfadqelgda pfldrlrrdq kslrgrgstl gldirtatre
 61 gkhiverile eesdealemt iasvpasryl temtleemsr dwlmlipkqk vtgplcirmd
121 qaimgkniil kanfsvifnr lealillraf tdegaivgei splpslpght dedvknaigv
181 ligglewndn tvrvsetlqr ftwrssdeng rsplppkqkr kvertiepev (SEQ ID NO: 10)

H3N2
  1 mdsntvssfq vdcflwhirk qvvdqelsda pfldrlrrdq rslrgrgrtl gldikaathv
 61 gkqivqkilk eesdealkmt mastpasryi tdmtieelsr nwfmlmpkqk vegplcirmd
121 qaimekniml kanfsvifdr letivllrgf teegaivgei splpsfpght iedvknaigv
181 ligglewndn tvrvsknlqr fawrssneng gppltpkqkr kmartarskv (SEQ ID NO: 11)

H5N1
  1 mdsntvssfq vdcflwrvrk rfadqelgda pfldrlrrdq kslrgrgstl gldirtatre
 61 gkhiverile eesdealkmt iasvpapryl temtleemsr dwlmlipkqk vtgslcirmd
121 qaimdkdiil kanfsvifnr lealillraf tdegaivgei splpslpght eedvknaigv
181 ligglewndn tvrvsetlqr ftwrssdeng rsplppkqkr kmertiepev (SEQ ID NO: 12)

B
  1 madnmtttqi evgpgatnat infeagilec yerlswqral dypgqdrlnr lkrklesrik
 61 thnksepesk rmsleerkai gvkmmkvllf mnpsagiegf epycmksssn sncpkynwtd
121 ypstpgrcld dieeepddvd gpteivlrdm nnkdarqkik eevntqkegk frltikrdir
181 nvlslrvlvn gtflkhpngy kslstlhrln aydqggrlva klvatdddltv edeedghril
241 nslferlneg hskpiraaet avgvlsqfgq ehrlspeegd n (SEQ ID NO: 13)

C
  1 mdsntvssfq vdcflwhirk rfadnglgda pfldrlrrdq kslkgrgstl gldietatlv
 61 gkqivewilk eesnetlkma iasvptsryl admtleemsr dwfmlmprqk itgslcvrmd
121 gaimekniil kanfsvifnr letlillraf teegaivgei splpslpght dedvknavgv
181 ligglewngn tvrvsenlqr fawrsrnedg rpslppeqk (SEQ ID NO: 14)

*FIG. 8B*

SEQUENCE LISTING

```
<160> NUMBER OF SEQ ID NOS: 33

<210> SEQ ID NO 1
<211> LENGTH: 122
<212> TYPE: PRT
<213> ORGANISM: Influenza virus

<400> SEQUENCE: 1

Met Ala Asp Asn Met Thr Thr Thr Gln Ile Glu Trp Arg Met Lys Lys
 1               5                  10                  15

Met Ala Ile Gly Ser Ser Thr His Ser Ser Ser Val Leu Met Lys Asp
                20                  25                  30

Ile Gln Ser Gln Phe Glu Gln Leu Lys Leu Arg Trp Glu Ser Tyr Pro
            35                  40                  45

Asn Leu Val Lys Ser Thr Asp Tyr His Gln Lys Arg Glu Thr Ile Arg
    50                  55                  60

Leu Ala Thr Glu Glu Leu Tyr Leu Leu Ser Lys Arg Ile Asp Asp Ser
65                  70                  75                  80

Ile Leu Phe His Lys Thr Val Ile Ala Asn Ser Ser Ile Ile Ala Asp
                85                  90                  95

Met Ile Val Ser Leu Ser Leu Leu Glu Thr Leu Tyr Glu Met Lys Asp
                100                 105                 110

Val Val Glu Val Tyr Ser Arg Gln Cys Leu
            115                 120

<210> SEQ ID NO 2
<211> LENGTH: 122
<212> TYPE: PRT
<213> ORGANISM: Influenza virus

<400> SEQUENCE: 2

Met Ala Asp Asn Met Thr Thr Thr Gln Ile Glu Trp Arg Met Lys Lys
 1               5                  10                  15

Met Ala Ile Gly Ser Ser Thr His Ser Ser Ser Val Leu Met Lys Asp
                20                  25                  30
```

```
Ile Gln Ser Gln Phe Glu Gln Leu Lys Leu Arg Trp Glu Ser Tyr Pro
            35                  40                  45
Asn Leu Val Lys Ser Thr Asp Tyr His Gln Lys Arg Glu Thr Ile Arg
         50                  55                  60
Leu Val Thr Glu Glu Leu Tyr Leu Leu Ser Lys Arg Ile Asp Asp Asn
 65                  70                  75                  80
Ile Leu Phe His Lys Thr Val Ile Ala Asn Ser Ser Ile Ile Ala Asp
                85                  90                  95
Met Ile Val Ser Leu Ser Leu Glu Thr Leu Tyr Glu Met Lys Asp
            100                 105                 110
Val Val Glu Val Tyr Ser Arg Gln Cys Leu
            115                 120
```

<210> SEQ ID NO 3
<211> LENGTH: 121
<212> TYPE: PRT
<213> ORGANISM: Influenza virus

<400> SEQUENCE: 3

```
Met Asp Ser Asn Thr Val Ser Ser Phe Gln Asp Ile Leu Met Arg Met
 1               5                   10                  15
Ser Lys Met Gln Leu Gly Ser Ser Ser Glu Asp Leu Asn Gly Met Ile
            20                  25                  30
Thr Gln Phe Glu Ser Leu Lys Leu Tyr Arg Asp Ser Leu Gly Glu Ala
         35                  40                  45
Val Met Arg Met Gly Asp Leu His Ser Leu Gln Asn Arg Asn Gly Lys
 50                  55                  60
Trp Arg Glu Gln Leu Ser Gln Lys Phe Glu Glu Ile Arg Trp Leu Ile
 65                  70                  75                  80
Glu Glu Val Arg His Arg Leu Lys Val Thr Glu Asn Ser Phe Glu Gln
                85                  90                  95
Ile Thr Phe Met Gln Ala Leu Gln Leu Leu Leu Glu Val Glu Gln Glu
            100                 105                 110
Ile Arg Thr Phe Ser Phe Gln Leu Ile
        115                 120
```

<210> SEQ ID NO 4
<211> LENGTH: 121
<212> TYPE: PRT
<213> ORGANISM: Influenza virus

<400> SEQUENCE: 4

```
Met Asp Ser Asn Thr Val Ser Ser Phe Gln Asp Ile Leu Thr Arg Met
 1               5                   10                  15
Ser Lys Met Gln Leu Gly Ser Ser Ser Glu Asp Leu Asn Gly Met Ile
            20                  25                  30
Thr Gln Phe Glu Ser Leu Lys Leu Tyr Arg Asp Ser Leu Gly Glu Ala
         35                  40                  45
Val Met Arg Met Gly Asp Leu His Ser Leu Gln Asn Arg Asn Gly Lys
 50                  55                  60
Trp Arg Glu Gln Leu Ser Gln Lys Phe Glu Glu Ile Arg Trp Leu Ile
 65                  70                  75                  80
Glu Glu Val Arg His Arg Leu Arg Ile Thr Glu Asn Ser Phe Glu Gln
                85                  90                  95
Ile Thr Phe Met Gln Ala Leu Gln Leu Leu Leu Glu Val Glu Gln Glu
            100                 105                 110
Ile Arg Thr Phe Ser Phe Gln Leu Ile
```

-continued

```
                115                 120

<210> SEQ ID NO 5
<211> LENGTH: 121
<212> TYPE: PRT
<213> ORGANISM: Influenza virus

<400> SEQUENCE: 5

Met Asp Ser Asn Thr Val Ser Ser Phe Gln Asp Ile Leu Leu Arg Met
1               5                   10                  15

Ser Lys Met Gln Leu Gly Ser Ser Ser Glu Asp Leu Asn Gly Met Ile
            20                  25                  30

Thr Gln Phe Glu Ser Leu Lys Ile Tyr Arg Asp Ser Leu Gly Glu Ala
        35                  40                  45

Val Met Arg Met Gly Asp Leu His Leu Leu Gln Asn Arg Asn Gly Lys
    50                  55                  60

Trp Arg Glu Gln Leu Gly Gln Lys Phe Glu Glu Ile Arg Trp Leu Ile
65                  70                  75                  80

Glu Glu Val Arg His Arg Leu Lys Thr Ile Glu Asn Ser Phe Glu Gln
                85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
        115                 120

<210> SEQ ID NO 6
<211> LENGTH: 121
<212> TYPE: PRT
<213> ORGANISM: Influenza virus

<400> SEQUENCE: 6

Met Asp Ser Asn Thr Val Ser Ser Phe Gln Asp Ile Leu Lys Arg Met
1               5                   10                  15

Ser Lys Met Gln Leu Gly Ser Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Gly Lys
    50                  55                  60

Trp Arg Glu Gln Leu Ser Gln Lys Phe Glu Glu Ile Arg Trp Leu Ile
65                  70                  75                  80

Glu Glu Val Arg His Arg Leu Arg Ile Thr Glu Asn Ser Phe Glu Gln
                85                  90                  95

Ile Thr Phe Met Gln Ala Leu Gln Leu Leu Leu Glu Val Glu Gln Glu
            100                 105                 110

Ile Arg Thr Phe Ser Phe Gln Leu Ile
        115                 120

<210> SEQ ID NO 7
<211> LENGTH: 182
<212> TYPE: PRT
<213> ORGANISM: Influenza virus

<400> SEQUENCE: 7

Met Ser Asp Lys Thr Val Lys Ser Thr Asn Leu Met Ala Phe Val Ala
1               5                   10                  15

Thr Lys Met Leu Glu Arg Gln Glu Asp Leu Asp Thr Cys Thr Glu Met
            20                  25                  30
```

-continued

```
Gln Val Glu Lys Met Lys Thr Ser Thr Lys Ala Arg Leu Arg Thr Glu
         35                  40                  45

Ser Ser Phe Ala Pro Arg Thr Trp Glu Asp Ala Ile Lys Asp Glu Ile
 50                  55                  60

Leu Arg Arg Ser Val Asp Thr Ser Ser Leu Asp Arg Trp Pro Glu Leu
 65                  70                  75                  80

Lys Gln Glu Leu Glu Asn Val Ser Asp Ala Leu Lys Ala Asp Ser Leu
                 85                  90                  95

Trp Leu Pro Met Lys Ser Leu Ser Leu Tyr Ser Glu Val Ser Asn Gln
                100                 105                 110

Glu Pro Ser Ser Ile Pro Ile Gly Glu Met Lys His Gln Ile Leu Thr
                115                 120                 125

Arg Leu Lys Leu Ile Cys Ser Arg Leu Glu Lys Leu Asp His Asn Leu
130                 135                 140

Ser Lys Ala Val Leu Gly Ile Gln Asn Ser Glu Asp Leu Ile Leu Ile
145                 150                 155                 160

Ile Tyr Asn Arg Asp Val Cys Lys Asn Thr Ile Leu Met Ile Lys Ser
                165                 170                 175

Leu Cys Asn Ser Leu Ile
                180
```

<210> SEQ ID NO 8
<211> LENGTH: 281
<212> TYPE: PRT
<213> ORGANISM: Influenza virus

<400> SEQUENCE: 8

```
Met Ala Asp Asn Met Thr Thr Thr Gln Ile Glu Val Gly Pro Gly Ala
 1               5                  10                  15

Thr Asn Ala Thr Ile Asn Phe Glu Ala Gly Ile Leu Glu Cys Tyr Glu
                 20                  25                  30

Arg Leu Ser Trp Gln Arg Ala Leu Asp Tyr Pro Gly Gln Asp Arg Leu
         35                  40                  45

Asn Arg Leu Lys Arg Lys Leu Glu Ser Arg Ile Lys Thr His Asn Lys
 50                  55                  60

Ser Glu Pro Glu Ser Lys Arg Met Ser Leu Glu Glu Arg Lys Ala Ile
 65                  70                  75                  80

Gly Val Lys Met Met Lys Val Leu Leu Phe Met Asp Pro Ser Ala Gly
                 85                  90                  95

Ile Glu Gly Phe Glu Pro Tyr Cys Met Lys Ser Ser Asn Ser Asn
                100                 105                 110

Cys Pro Lys Tyr Asn Trp Thr Asp Tyr Pro Ser Thr Pro Gly Arg Cys
                115                 120                 125

Leu Asp Asp Ile Glu Glu Glu Pro Glu Asp Val Asp Gly Pro Thr Glu
130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Thr Arg Leu Thr Ile Lys
                165                 170                 175

Arg Asp Ile Arg Asn Val Leu Ser Leu Arg Val Leu Val Asn Gly Thr
                180                 185                 190

Phe Leu Lys His Pro Asn Gly Tyr Lys Ser Leu Ser Thr Leu His Arg
                195                 200                 205

Leu Asn Ala Tyr Asp Gln Ser Gly Arg Leu Val Ala Lys Leu Val Ala
210                 215                 220
```

```
Thr Asp Asp Leu Thr Val Glu Asp Glu Glu Asp Gly His Arg Ile Leu
225                 230                 235                 240

Asn Ser Leu Phe Glu Arg Leu Asn Glu Gly His Pro Lys Pro Ile Arg
            245                 250                 255

Ala Ala Glu Thr Ala Val Gly Val Leu Ser Gln Phe Gly Gln Glu His
        260                 265                 270

Arg Leu Ser Pro Glu Glu Gly Asp Asn
        275                 280
```

<210> SEQ ID NO 9
<211> LENGTH: 230
<212> TYPE: PRT
<213> ORGANISM: Influenza virus

<400> SEQUENCE: 9

```
Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
50                  55                  60

Val Glu Arg Ile Leu Glu Glu Ser Asp Glu Ala Leu Lys Met Thr
65                  70                  75                  80

Ile Ala Ser Val Pro Ala Ser Arg Tyr Leu Thr Asp Met Thr Leu Glu
                85                  90                  95

Glu Met Ser Arg Asp Trp Phe Met Leu Met Pro Lys Gln Lys Val Ala
            100                 105                 110

Gly Ser Leu Cys Ile Arg Met Asp Gln Ala Ile Met Asn Lys Asn Ile
        115                 120                 125

Ile Leu Lys Ala Asn Phe Ser Val Ile Phe Asp Arg Leu Glu Thr Leu
130                 135                 140

Ile Leu Leu Arg Ala Phe Thr Glu Glu Gly Ala Ile Ile Gly Glu Ile
145                 150                 155                 160

Ser Pro Leu Pro Ser Leu Pro Gly His Thr Asp Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asp Gly Arg Pro Pro Leu Pro Pro Lys Gln Lys Arg Lys Met Ala Arg
210                 215                 220

Thr Ile Glu Ser Glu Val
225                 230
```

<210> SEQ ID NO 10
<211> LENGTH: 230
<212> TYPE: PRT
<213> ORGANISM: Influenza virus

<400> SEQUENCE: 10

```
Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
```

```
                35                  40                  45
Thr Leu Gly Leu Asp Ile Arg Thr Ala Thr Arg Glu Gly Lys His Ile
 50                  55                  60

Val Glu Arg Ile Leu Glu Glu Ser Asp Glu Ala Leu Glu Met Thr
 65                  70                  75                  80

Ile Ala Ser Val Pro Ala Ser Arg Tyr Leu Thr Glu Met Thr Leu Glu
                 85                  90                  95

Glu Met Ser Arg Asp Trp Leu Met Leu Ile Pro Lys Gln Lys Val Thr
                100                 105                 110

Gly Pro Leu Cys Ile Arg Met Asp Gln Ala Ile Met Gly Lys Asn Ile
                115                 120                 125

Ile Leu Lys Ala Asn Phe Ser Val Ile Phe Asn Arg Leu Glu Ala Leu
            130                 135                 140

Ile Leu Leu Arg Ala Phe Thr Asp Glu Gly Ala Ile Val Gly Glu Ile
145                 150                 155                 160

Ser Pro Leu Pro Ser Leu Pro Gly His Thr Asp Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
            195                 200                 205

Asn Gly Arg Ser Pro Leu Pro Pro Lys Gln Lys Arg Lys Val Glu Arg
            210                 215                 220

Thr Ile Glu Pro Glu Val
225                 230

<210> SEQ ID NO 11
<211> LENGTH: 230
<212> TYPE: PRT
<213> ORGANISM: Influenza virus

<400> SEQUENCE: 11

Met Asp Ser Asn Thr Val Ser Ser Phe Gln Val Asp Cys Phe Leu Trp
 1               5                  10                  15

His Ile Arg Lys Gln Val Val Asp Gln Glu Leu Ser Asp Ala Pro Phe
                20                  25                  30

Leu Asp Arg Leu Arg Arg Asp Gln Arg Ser Leu Arg Gly Arg Gly Arg
            35                  40                  45

Thr Leu Gly Leu Asp Ile Lys Ala Ala Thr His Val Gly Lys Gln Ile
 50                  55                  60

Val Gln Lys Ile Leu Lys Glu Glu Ser Asp Glu Ala Leu Lys Met Thr
 65                  70                  75                  80

Met Ala Ser Thr Pro Ala Ser Arg Tyr Ile Thr Asp Met Thr Ile Glu
                 85                  90                  95

Glu Leu Ser Arg Asn Trp Phe Met Leu Met Pro Lys Gln Lys Val Glu
                100                 105                 110

Gly Pro Leu Cys Ile Arg Met Asp Gln Ala Ile Met Glu Lys Asn Ile
                115                 120                 125

Met Leu Lys Ala Asn Phe Ser Val Ile Phe Asp Arg Leu Glu Thr Ile
            130                 135                 140

Val Leu Leu Arg Gly Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
```

```
                180                 185                 190
Arg Val Ser Lys Asn Leu Gln Arg Phe Ala Trp Arg Ser Ser Asn Glu
        195                 200                 205

Asn Gly Gly Pro Pro Leu Thr Pro Lys Gln Lys Arg Lys Met Ala Arg
210                 215                 220

Thr Ala Arg Ser Lys Val
225                 230

<210> SEQ ID NO 12
<211> LENGTH: 230
<212> TYPE: PRT
<213> ORGANISM: Influenza virus

<400> SEQUENCE: 12

Met Asp Ser Asn Thr Val Ser Ser Phe Gln Val Asp Cys Phe Leu Trp
1               5                   10                  15

Arg Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Ser Asp Glu Ala Leu Lys Met Thr
65                  70                  75                  80

Ile Ala Ser Val Pro Ala Pro Arg Tyr Leu Thr Glu Met Thr Leu Glu
                85                  90                  95

Glu Met Ser Arg Asp Trp Leu Met Leu Ile Pro Lys Gln Lys Val Thr
            100                 105                 110

Gly Ser Leu Cys Ile Arg Met Asp Gln Ala Ile Met Asp Lys Asp Ile
        115                 120                 125

Ile Leu Lys Ala Asn Phe Ser Val Ile Phe Asn Arg Leu Glu Ala Leu
    130                 135                 140

Ile Leu Leu Arg Ala Phe Thr Asp Glu Gly Ala Ile Val Gly Glu Ile
145                 150                 155                 160

Ser Pro Leu Pro Ser Leu Pro Gly His Thr Glu Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205

Asn Gly Arg Ser Pro Leu Pro Pro Lys Gln Lys Arg Lys Met Glu Arg
210                 215                 220

Thr Ile Glu Pro Glu Val
225                 230

<210> SEQ ID NO 13
<211> LENGTH: 281
<212> TYPE: PRT
<213> ORGANISM: Influenza virus

<400> SEQUENCE: 13

Met Ala Asp Asn Met Thr Thr Thr Gln Ile Glu Val Gly Pro Gly Ala
1               5                   10                  15

Thr Asn Ala Thr Ile Asn Phe Glu Ala Gly Ile Leu Glu Cys Tyr Glu
            20                  25                  30

Arg Leu Ser Trp Gln Arg Ala Leu Asp Tyr Pro Gly Gln Asp Arg Leu
        35                  40                  45
```

Asn Arg Leu Lys Arg Lys Leu Glu Ser Arg Ile Lys Thr His Asn Lys
    50                  55                  60

Ser Glu Pro Glu Ser Lys Arg Met Ser Leu Glu Arg Lys Ala Ile
65                  70                  75                  80

Gly Val Lys Met Met Lys Val Leu Leu Phe Met Asn Pro Ser Ala Gly
                85                  90                  95

Ile Glu Gly Phe Glu Pro Tyr Cys Met Lys Ser Ser Asn Ser Asn
            100                 105                 110

Cys Pro Lys Tyr Asn Trp Thr Asp Tyr Pro Ser Thr Pro Gly Arg Cys
        115                 120                 125

Leu Asp Asp Ile Glu Glu Pro Asp Val Asp Gly Pro Thr Glu
        130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Gly Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280

<210> SEQ ID NO 14
<211> LENGTH: 219
<212> TYPE: PRT
<213> ORGANISM: Influenza virus

<400> SEQUENCE: 14

Met Asp Ser Asn Thr Val Ser Ser Phe Gln Val Asp Cys Phe Leu Trp
1               5                   10                  15

His Ile Arg Lys Arg Phe Ala Asp Asn Gly Leu Gly Asp Ala Pro Phe
            20                  25                  30

Leu Asp Arg Leu Arg Arg Asp Gln Lys Ser Leu Lys Gly Arg Gly Ser
        35                  40                  45

Thr Leu Gly Leu Asp Ile Glu Thr Ala Thr Leu Val Gly Lys Gln Ile
    50                  55                  60

Val Glu Trp Ile Leu Lys Glu Glu Ser Asn Glu Thr Leu Lys Met Ala
65                  70                  75                  80

Ile Ala Ser Val Pro Thr Ser Arg Tyr Leu Ala Asp Met Thr Leu Glu
                85                  90                  95

Glu Met Ser Arg Asp Trp Phe Met Leu Met Pro Arg Gln Lys Ile Thr
            100                 105                 110

Gly Ser Leu Cys Val Arg Met Asp Gln Ala Ile Met Glu Lys Asn Ile
        115                 120                 125

Ile Leu Lys Ala Asn Phe Ser Val Ile Phe Asn Arg Leu Glu Thr Leu
    130                 135                 140

```
Ile Leu Leu Arg Ala Phe Thr Glu Glu Gly Ala Ile Val Gly Glu Ile
145                 150                 155                 160

Ser Pro Leu Pro Ser Leu Pro Gly His Thr Asp Glu Asp Val Lys Asn
                165                 170                 175

Ala Val Gly Val Leu Ile Gly Gly Leu Glu Trp Asn Gly Asn Thr Val
            180                 185                 190

Arg Val Ser Glu Asn Leu Gln Arg Phe Ala Trp Arg Ser Arg Asn Glu
        195                 200                 205

Asp Gly Arg Pro Ser Leu Pro Pro Glu Gln Lys
    210                 215
```

<210> SEQ ID NO 15
<211> LENGTH: 16
<212> TYPE: PRT
<213> ORGANISM: Influenza virus

<400> SEQUENCE: 15

```
Glu Gln Leu Gly Gln Lys Phe Glu Glu Ile Arg Trp Leu Ile Glu Glu
1               5                   10                  15
```

<210> SEQ ID NO 16
<211> LENGTH: 14
<212> TYPE: PRT
<213> ORGANISM: Influenza virus

<400> SEQUENCE: 16

```
Lys Gln Lys Arg Lys Met Ala Gly Thr Ile Arg Ser Glu Val
1               5                   10
```

<210> SEQ ID NO 17
<211> LENGTH: 16
<212> TYPE: PRT
<213> ORGANISM: Influenza virus

<400> SEQUENCE: 17

```
Glu Gln Leu Gly Gln Lys Phe Glu Glu Ile Arg Ser Leu Ile Glu Glu
1               5                   10                  15
```

<210> SEQ ID NO 18
<211> LENGTH: 16
<212> TYPE: PRT
<213> ORGANISM: Influenza virus

<400> SEQUENCE: 18

```
Glu Gln Leu Gly Gln Lys Phe Glu Ser Ile Arg Trp Leu Ile Glu Glu
1               5                   10                  15
```

<210> SEQ ID NO 19
<211> LENGTH: 16
<212> TYPE: PRT
<213> ORGANISM: Influenza virus

<400> SEQUENCE: 19

```
Ser Gln Leu Gly Gln Lys Phe Ser Glu Ile Arg Trp Leu Ile Glu Glu
1               5                   10                  15
```

<210> SEQ ID NO 20
<211> LENGTH: 21
<212> TYPE: PRT
<213> ORGANISM: Influenza virus

<400> SEQUENCE: 20

```
Lys Gln Lys Arg Lys Met Ala Val Ala Ile Arg Ser Glu Val Phe Gly
```

```
                1               5                  10                 15
Asn Lys Met Val Asp
            20

<210> SEQ ID NO 21
<211> LENGTH: 16
<212> TYPE: PRT
<213> ORGANISM: Influenza virus

<400> SEQUENCE: 21

Ser Gln Leu Gly Gln Lys Phe Ser Ser Ile Arg Trp Leu Ile Glu Glu
  1               5                  10                 15

<210> SEQ ID NO 22
<211> LENGTH: 21
<212> TYPE: PRT
<213> ORGANISM: Influenza virus

<400> SEQUENCE: 22

Lys Gln Lys Arg Lys Met Ala Val Ala Ile Arg Ser Glu Val Phe Val
  1               5                  10                 15

Asp Lys Met Val Asp
            20

<210> SEQ ID NO 23
<211> LENGTH: 21
<212> TYPE: PRT
<213> ORGANISM: Influenza virus

<400> SEQUENCE: 23

Lys Gln Lys Arg Lys Met Ala Arg Thr Ala Arg Ser Lys Val Arg Arg
  1               5                  10                 15

Asp Lys Met Ala Asp
            20

<210> SEQ ID NO 24
<211> LENGTH: 16
<212> TYPE: PRT
<213> ORGANISM: Influenza virus

<400> SEQUENCE: 24

Glu Thr Ile Arg Leu Ala Thr Glu Glu Leu Tyr Leu Leu Ser Lys Arg
  1               5                  10                 15

<210> SEQ ID NO 25
<211> LENGTH: 63
<212> TYPE: DNA
<213> ORGANISM: Artificial Sequence
<220> FEATURE:
<223> OTHER INFORMATION: A synthetic oligonucleotide

<400> SEQUENCE: 25
gagagacgtc tcgaaataag aagcttgatt gaagaagtga gacacaaact gaagataaca      60
gag                                                                    63

<210> SEQ ID NO 26
<211> LENGTH: 46
<212> TYPE: DNA
<213> ORGANISM: Artificial Sequence
<220> FEATURE:
<223> OTHER INFORMATION: A synthetic oligonucleotide

<400> SEQUENCE: 26
gagagacgtc tctatttctt caaacttctg acctaattgt tcccgc                     46
```

```
<210> SEQ ID NO 27
<211> LENGTH: 61
<212> TYPE: DNA
<213> ORGANISM: Artificial Sequence
<220> FEATURE:
<223> OTHER INFORMATION: A synthetic oligonucleotide

<400> SEQUENCE: 27
gagagacgtc tcctgaccta attgcgaccg ccattttccg tttctgtttt ggagtgagtg      60
g                                                                     61

<210> SEQ ID NO 28
<211> LENGTH: 66
<212> TYPE: DNA
<213> ORGANISM: Artificial Sequence
<220> FEATURE:
<223> OTHER INFORMATION: A synthetic oligonucleotide

<400> SEQUENCE: 28
gagagacgtc tcggtcagaa gttttcggaa ataagatggt tgattgaaga agtgagacac      60
agactg                                                                66

<210> SEQ ID NO 29
<211> LENGTH: 61
<212> TYPE: DNA
<213> ORGANISM: Artificial Sequence
<220> FEATURE:
<223> OTHER INFORMATION: A synthetic oligonucleotide

<400> SEQUENCE: 29
gagagacgtc tcctgaccta attgcgaccg ccattttccg tttctgtttt ggagtgagtg      60
g                                                                     61

<210> SEQ ID NO 30
<211> LENGTH: 66
<212> TYPE: DNA
<213> ORGANISM: Artificial Sequence
<220> FEATURE:
<223> OTHER INFORMATION: A synthetic oligonucleotide

<400> SEQUENCE: 30
gagagacgtc tcggtcagaa gttttcgtcg ataagatggt tgattgaaga agtgagacac      60
agactg                                                                66

<210> SEQ ID NO 31
<211> LENGTH: 7
<212> TYPE: PRT
<213> ORGANISM: Influenza virus

<400> SEQUENCE: 31

Phe Gly Asn Lys Met Val Asp
 1               5

<210> SEQ ID NO 32
<211> LENGTH: 7
<212> TYPE: PRT
<213> ORGANISM: Influenza virus

<400> SEQUENCE: 32

Phe Val Asp Lys Met Val Asp
 1               5
```

```
<210> SEQ ID NO 33
<211> LENGTH: 5
<212> TYPE: PRT
<213> ORGANISM: Influenza virus

<400> SEQUENCE: 33

Arg Lys Leu Lys Arg
 1               5
```

US 8,507,247 B2

INFLUENZA A VIRUS WITH ATTENUATING MUTATIONS IN NS2 PROTEIN

CROSS-REFERENCE TO RELATED APPLICATIONS

This patent application claims the benefit of priority, under 35 U.S.C. §119(e), to U.S. Provisional Patent Application Ser. No. 61/273,956, filed on Aug. 11, 2009, the disclosure of which is incorporated by reference herein in its entirety.

STATEMENT OF GOVERNMENT RIGHTS

This invention was made with government support under AI47446 awarded by the National Institutes of Health. The government has certain rights in the invention.

BACKGROUND

The influenza A virus can undergo transcription and replication entirely inside the nucleus. The newly synthesized viral ribonucleoproteins (vRNPs) are later exported for incorporation into virions at the plasma membrane (Nayak et al., 2004). The viral proteins NS1 and NS2, designated as non-structural (NS) proteins in early studies (Lamb and Choppin, 1983), are both encoded by the smallest influenza virus segment, segment 8 (Inglis et al., 1979; Lamb et al., 1980).

NS1 has multiple functions during virus infection (Krug et al., 2003), including the inhibition of the early interferon-α/β-independent (IFN-α/β) antiviral response of cells by blocking the posttranscriptional processing of cellular antiviral pre-mRNAs (Fortes et al., 1994; Kim et al., 2008). The C-terminal domain of NS1, named the effector domain, binds the 30 kDa subunit of the cleavage and polyadenylation specificity factor (CPSF) (Meveroff et al., 1998) and the poly(A)-binding protein II (PABII) via residues 223-237 (Chen et al., 1999). These binding events prevent processing of the 3' ends of cellular pre-mRNAs and thus their nuclear export. The C-terminal domain also directly targets the export machinery and the nuclear pore complex (Satterly et al., 2007). NS1 also blocks the cellular antiviral response mediated by protein kinase R (PKR) (Bergmann et al., 2000; Hatada et al., 1999; Lu et al., 1997) by direct binding to that protein (Tan and Katze, 1998). It also enhances the translation of the viral mRNAs (de la Luna et al., 1995; Enami et al., 1994; Park and Katze, 1995), and shuts off cellular protein synthesis, by interacting with the eukaryotic translational factor 4GI (eIF4GI) (Aragon et al., 2000; Burgui et al., 2003) and possibly with the host mRNA binding protein guanine-rich sequence factor 1 (GRSF-1) (Park et al., 1999).

Relative to NS1, the NS2 protein is much less well characterized. Although NS2 was initially designated as a nonstructural protein (Lamb et al., 1980), it has been shown to exist in purified viral particles (Richardson and Akkina, 1991). NS2 also accumulates preferentially in the nuclei of infected eukaryotic cells (Greenspan et al., 1985; Smith et al., 1987). Some studies have suggested a role for NS2 in regulating viral RNA replication (Bullido et al., 2001; Odagiri et al., 1990; Odagiri et al., 1994), thereby providing a possible explanation for its nuclear accumulation. The function of NS2 during the viral cycle became more apparent when O'Neill and colleagues (O'Neill et al., 1998) showed that NS2 was the adaptor between the cellular nuclear export machinery Crm1 and the newly amplified viral genomic segments (vRNPs). They then renamed NS2 nuclear export protein (NEP).

The central role of NS2/NEP in vRNP nuclear export through Crm1 was later confirmed by in vivo (Iwatsuki-Norimoto et al., 2004; Neumann et al., 2006) and in vitro (Akarsu et al., 2003) studies. Conflicting data, however, have also been published, where the viral matrix protein M1 was sufficient for the nuclear export of vRNPs in the absence of NS2/NEP (Bui et al., 2000) and the viral nucleoprotein NP interacted directly with Crm1 (Elton et al., 2001). Nevertheless, the studies showing the interaction of NS2/NEP with Crm1 (Akarsu et al., 2003; Neumann et al., 2000; O'Neill et al., 1995) and with M1 (Akarsu et al., 2003; Yasuda et al., 1993) and of M1 with the vRNPs (Baudin et al., 2001; Bui et al., 2000) suggest the following model for the nuclear export of the newly synthesized vRNPs: the C-terminal segment of M1 binds to NP, which associates with the vRNA, and the nuclear localization signal (NLS) in the N-terminus terminus of M1 binds to the C-terminal region of NS2/NEP. In turn, the N-terminal region of NS2/NEP recognizes Crm1 and permits the nuclear export of the vRNPs (Boulo et al., 2007).

SUMMARY OF THE INVENTION

The present invention relates to mutated influenza viruses that grow normally in cell culture but whose growth is attenuated, e.g., in mice. The invention provides an isolated attenuated influenza virus comprising a gene segment comprising a mutant NS2 protein gene and a live vaccine comprising that virus, and optionally having at least one other influenza virus strain, e.g., an influenza A virus strain or an influenza B virus strain. In one embodiment, the attenuated influenza virus is a recombinant influenza virus having a mutant NS2 protein with at least one substitution that alters in vivo but not in vitro properties of the virus, e.g., by replacing an amino acid residue that has an aromatic side chain with a residue with an aliphatic side chain, amide-containing side chain, basic side chain, or sulfur containing side chain (a nonconservative substitution). In one embodiment, the attenuated influenza virus is a recombinant influenza virus having a mutant NS2 protein with at least one substitution that alters in vivo but not in vitro properties of the virus, e.g., by replacing an amino acid residue that is negatively charged with neutral or positively charged residues (a nonconservative substitution). In one embodiment, the at least one substitution that alters in vivo but not in vitro properties of the virus is at a position corresponding to position 78 in influenza A virus NS2. In one embodiment, the at least one substitution is at a position corresponding to position 67, 74, 75, 81, or 82 in influenza A virus NS2. In one embodiment, the attenuated recombinant virus of the invention has at least two substitutions in influenza A virus NS2 that do not substantially alter the in vitro replication of the virus but are associated with attenuation of the virus in vivo. In one embodiment, the mutation in the NS2 gene results in one or more substitutions in the influenza virus NS2 protein, e.g., the mutants are E67S/E74S and E67S/E74S/E75S mutants, and may result in the addition of residues, e.g., seven amino acids, to the C-terminus of NS1 (due to gene overlap between NS2 and NS1, which are splice variants of the same transcript). In one embodiment, the recombinant virus has a mutant NS2 protein that may have altered binding to M1 but does not substantially alter the binding of NS1 to CPSF, PABII, PKR, GRSF-1 or eIF4GI, or any combination thereof. In one embodiment, at least one of the substitutions in NS2 is a substitution for glutamate. In one embodiment, at least one of the substitutions in NS2 is a substitution for tryptophan. In one embodiment, the mutation in the NS2 gene does not alter the coding region for NS1. In one embodiment, the mutation in the NS2 gene alters the coding region for NS1, e.g., resulting in at least one amino acid substitution in, or altering the reading frame for, e.g., by extending the 3' end of the open reading frame, NS1. In one embodiment, the mutation in the NS2 gene alters the reading frame for NS1, e.g., by extending the open reading frame by one or more amino acids, e.g., 1 to 20, or any integer in between 1 to 20, amino acids, at the C-terminus. In one embodiment, the isolated attenuated influenza virus is a type A virus. In one embodiment, the isolated attenuated influenza virus is a type B virus.

As described hereinbelow, mutations in the influenza A virus NS2 protein did not affect virus growth in cell culture. When mice were inoculated intranasally with $10^5$ PFU of such attenuated mutant viruses, there was no weight loss, whereas the wild-type virus caused death in 50% of the mice within 9 days. Mice were immunized intranasally with one of the mutant strains (E67S/E75S) and challenged 25 days later with 10 $LD_{50}$ of wild-type WSN virus. All of the immunized mice survived lethal WSN challenge and no virus was recovered from the lungs of the challenged mice. Thus, mutations in the NS2 may not affect virus replication in cell culture, but may confer an attenuated phenotype in mice. In addition, NS genes are highly conserved among influenza virus strains and may mutate less frequently than viral genes/proteins under selection pressure, such as the hemagglutin (HA) and neuraminidase (NA) surface glycoproteins and the ion channel protein M2. Thus, viruses with NS2 mutations, e.g., glutamate substitution mutants, are ideal candidates for the development of live attenuated vaccines.

In one embodiment, the attenuated recombinant influenza virus comprises a mutant NS2 protein gene which comprises one or more mutations, e.g., comprises at least two mutations, relative to a corresponding wild-type NS2 protein gene, wherein at least one of the mutations results in a substitution of a residue corresponding to a glutamate or a tryptophan residue in NS2 of influenza virus A. In one embodiment, the mutant NS gene segment, e.g., one encoding one or more substitutions in NS2 and/or one or more substitutions and/or additional residues at the C-terminus of NS1, when transcribed and translated in a cell yields detectable NS2 and/or NS1 protein, e.g., at least about 10%, 50%, or more, the levels of the corresponding wild-type NS2 or NS1 protein, respectively. In one embodiment, the substitution(s) in the NS2 protein is/are at or within about 1 to 10 residues, or any integer in between, for instance, at or within 1 to 5, residues, of residue 75 of the NS2 protein of influenza A virus. In one embodiment, the mutant NS1 protein gene has at least one substitution at or within about 1 to 10 residues, or any integer in between, e.g., at or within 1 to 5 residues of the codon for residue 224 of the NS2 protein of influenza A virus. In one embodiment, the mutant NS protein gene comprises one or more deletions of one or more nucleotides, at or, e.g., within about 120 nucleotides, e.g., at or within 1, 2, 3 up to 120 nucleotides, or any integer in between, in the coding region of the gene. In one embodiment, the mutant NS protein gene comprises one or more insertions of one or more nucleotides, at or, e.g., within about 120 nucleotides, e.g., at or within 1, 2, 3 up to 120 nucleotides, or any integer in between, in the coding region of the gene. Such insertion(s) and/or deletion(s) may alter the reading frame for the NS protein(s) gene. In yet another embodiment, the mutant NS2 protein gene comprises two or more mutations, e.g., two or more mutations including two or more amino acid substitutions, one of which is a substitution for at least one glutamate and optionally also a substitution for a tryptophan, substitution(s) that result in attenuation of virus with genes encoding the mutant NS protein(s).

Further provided is a method to prepare attenuated recombinant influenza viruses. The method includes contacting a host cell with a plurality of vectors including a vector for vRNA production comprising a promoter operably linked to an influenza virus PA cDNA linked to a transcription termination sequence, a vector for vRNA production comprising a promoter operably linked to an influenza virus PB1 cDNA linked to a transcription termination sequence, a vector for vRNA production comprising a promoter operably linked to an influenza virus PB2 cDNA linked to a transcription termination sequence, a vector for vRNA production comprising a promoter operably linked to an influenza virus HA cDNA linked to a transcription termination sequence, a vector for vRNA production comprising promoter operably linked to an influenza virus NP cDNA linked to a transcription termination sequence, a vector for vRNA production comprising a promoter operably linked to an influenza virus NA cDNA linked to a transcription termination sequence, a vector for vRNA production comprising a promoter operably linked to an influenza virus M cDNA linked to a transcription termination sequence, a vector for vRNA production comprising a promoter operably linked to an influenza virus NS cDNA linked to a transcription termination sequence, wherein the NS cDNA comprises mutant NS2 protein DNA which encodes a mutant NS2 protein that does not substantially alter the in vitro replication of the virus but is associated with attenuation of the virus in vivo as a result of one or more substitutions in NS2, and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, and a vector for mRNA production comprising a promoter operably linked to a DNA segment encoding influenza virus NS2. In one embodiment, at least one substitution is at a position corresponding to residue E67, residue E74, residue E75, residue E81 or residue E82 in influenza A virus NS2. In one embodiment, the substitution for glutamate is a substitution to serine, alanine, methionine, glycine, leucine, threonine, isoleucine, or valine. In one embodiment, the second substitution is a substitution for tryptophan at a position corresponding to residue 78 in influenza A virus NS2. In one embodiment, the mutation results in a mutant NS1 protein. In one embodiment, the mutant NS1 has one or more additional amino acid residues at the C-terminus. In one embodiment, the mutant NS1 has one or more amino acid substitutions. In one embodiment, the DNAs for vRNA production are from different influenza virus isolates.

Further provided is a composition comprising a plurality of influenza vectors. The composition includes a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the NS DNA comprises mutant NS2 protein DNA, wherein the mutant NS2 protein has at least two substitutions that do not substantially alter the in vitro replication of the virus but are associated with attenuation of the virus in vivo, wherein at least one of the substitutions is a substitution for glutamate; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding an ion channel protein, and a vector for mRNA production comprising a promoter operably linked to a DNA segment encoding influenza virus NS2.

Also provided method to prepare attenuated recombinant influenza virus. The method includes contacting a host cell with a plurality of vectors including a vector for vRNA production comprising a promoter operably linked to an influenza virus PA cDNA linked to a transcription termination sequence, a vector for vRNA production comprising a promoter operably linked to an influenza virus PB1 cDNA linked to a transcription termination sequence, a vector for vRNA production comprising a promoter operably linked to an influenza virus PB2 cDNA linked to a transcription termination sequence, a vector for vRNA production comprising a promoter operably linked to an influenza virus HA cDNA linked to a transcription termination sequence, a vector for vRNA production comprising promoter operably linked to an influenza virus NP cDNA linked to a transcription termination sequence, a vector for vRNA production comprising a promoter operably linked to an influenza virus NA and NB cDNA linked to a transcription termination sequence, a vector for vRNA production comprising a promoter operably linked to an influenza virus M cDNA linked to a transcription termination sequence, a vector for vRNA production comprising a promoter operably linked to an influenza virus NS cDNA linked to a transcription termination sequence, wherein the NS cDNA comprises mutant NS2 protein DNA which encodes a mutant NS2 protein that does not substantially alter the in vitro replication of the virus but is associated with attenuation of the virus in vivo as a result of one or more substitutions in NS2 and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, and a vector for mRNA production comprising a promoter operably linked to a DNA segment encoding influenza virus NS2.

Hence, the invention provides vectors, e.g., plasmids, which encode influenza virus proteins, and/or encode influenza vRNA, both native and recombinant vRNA and compositions comprising one or more of the vectors. Thus, a vector of the invention may encode an influenza virus protein (sense) or vRNA. A plurality of the vectors of the invention may be physically linked or each vector may be present on an individual plasmid or other, e.g., linear, nucleic acid delivery vehicle.

A composition of the invention may also comprise a gene or open reading frame of interest, e.g., a foreign gene encoding an immunogenic peptide or protein useful as a vaccine. Thus, another embodiment of the invention comprises a composition of the invention as described above in which one of the influenza virus genes in the vectors is replaced with a foreign gene, or the composition further comprises, in addition to all the influenza virus genes, a vector comprising a promoter linked to 5' influenza virus sequences linked to a desired nucleic acid sequence, e.g., a DNA of interest, linked to 3' influenza virus sequences linked to a transcription termination sequence, which, when contacted with a host cell permissive for influenza virus replication optionally results in recombinant virus. In one embodiment, the DNA of interest is in an antisense orientation. The DNA of interest, whether in a vector for vRNA or protein production, may encode an immunogenic epitope, such as an epitope useful in a cancer therapy or vaccine, or a peptide or polypeptide useful in gene therapy.

Any suitable promoter or transcription termination sequence may be employed to express a protein or peptide, e.g., a viral protein or peptide, a protein or peptide of a nonviral pathogen, or a therapeutic protein or peptide. In one embodiment, to express vRNA, the promoter is a RNA polymerase I promoter, a RNA polymerase II promoter, a RNA polymerase III promoter, a T3 promoter or a T7 promoter. Optionally the vector comprises a transcription termination sequence such as a RNA polymerase I transcription termination sequence, a RNA polymerase II transcription termination sequence, a RNA polymerase III transcription termination sequence, or a ribozyme.

The invention also provides a method to prepare influenza virus. The method comprises contacting a cell, e.g., an avian or a mammalian cell, with the isolated virus of the invention or a plurality of the vectors of the invention, e.g., sequentially or simultaneously, for example, employing a composition comprising a plurality of the vectors, in an amount effective to yield infectious influenza virus. The invention also includes isolating virus from a cell infected with the virus or contacted with the vectors. The invention further provides a host cell infected with the virus of the invention or contacted with the vectors. In one embodiment, a host cell is infected with an attenuated (e.g., cold adapted) donor virus and a virus of the invention to prepare a cold-adapted reassortant virus useful as a cold-adapted live virus vaccine.

The invention further provides a vaccine or immunogenic composition comprising at least one recombinant virus of the invention, and a method of using the vaccine or immunogenic composition to immunize a vertebrate or induce an immune response in a vertebrate, respectively. The influenza vaccine may employed with other anti-virals, e.g., amantadine, rimantadine, and/or neuraminidase inhibitors, e.g., may be administered separately in conjunction with those anti-virals, for instance, administered before, during and/or after viral infection.

The method includes administering, e.g., intranasally or intramuscularly, to the vertebrate, e.g., an avian or a mammal such as a human, a composition comprising an effective amount of the attenuated recombinant virus of the invention. In one embodiment, the recombinant virus of the invention includes genes from influenza A virus. In another embodiment, the recombinant virus of the invention includes genes from influenza B virus. In yet another embodiment, the recombinant virus of the invention includes genes from influenza C virus. In a further embodiment, the recombinant virus of the invention includes one or more genes from influenza A virus, influenza B virus, influenza C virus, or any combination thereof. For instance, the recombinant virus may comprise a mutant NS gene derived from the NS gene of A/Chicken/Jalagon/12419/2006, A/Chicken/British Columbia/GSC_human_B104, A/Hong Kong/1074/901, A/Hong Kong/498197, A/Hong Kong/97198, A/Wisconsin/4755/1994, C/Yamagata/1/88, B/Lee/40, B/AnnArbor/1/1986, B/Yamanashi/166/98, B/Cheongju/411/2000, B/Shiga/T30/98, B/Mie/1/93, B/Chiba/447/98, B/Victoria/2/87, B/Yamanashi/166/98, B/Nagoya/20/99, B/Kouchi/193/99, B/Saga/S172/99, B/Kanagawa, B/Lusaka/432/99, B/Lusaka/270/99, B/Quebec/74204/99, B/Quebec/453/98, B/Quebec/51/98, B/Quebec/465/98 and B/Quebec/511/98 (Accession Nos. FJ010995, ABG85185, ABF21221, AAD29244, AAT78587, AAT78588, AAK49299, AAK49300, BAC54000, BAC54011, AAK18009, AAK18010, AAK49317, AAK49318, BAA19602, ACJ53911, AAB03300, AB036873, AB03672, AB036871, AB036870, AB036869, AB036868, AB036867, AB036866, D14855, D14543, D14542, AB059251, AB059243, NC 002209, AJ419127, AJ419126, AJ419125, AJ419124, and AJ419123, the disclosures of which are specifically incorporated by reference herein). In one embodiment, the mutation(s) in the NS2 gene do not alter the sequence of the NS1 gene. In another embodiment, the mutation(s) in the NS2 gene also alter(s) the sequence of the NS1 gene but yield(s) NS proteins with substantially the same intracellular localization as the NS proteins encoded by a corresponding non-mutated NS gene.

In one embodiment, the isolated attenuated recombinant influenza virus of the invention has a nonconservative substitution at a residue corresponding to residue 78 of NS2 of influenza A virus, e.g., a tryptophan to a serine substitution, a nonconservative substitution at one of residues corresponding to residue 67, 74, 75, 81 or 82 of NS2 of influenza A virus, e.g., a glutamate to a serine substitution at one of those residues. In one embodiment, the isolated attenuated recombinant influenza virus of the invention has a residue other than glutamate or serine at residue 67, e.g., a nonconservative substitution for glutamate at residue 67, a residue other than glutamate or serine at residue 74, e.g., a nonconservative substitution for glutamate or serine at residue 74, a residue other than glutamate or serine at residue 75, e.g., a nonconservative substitution for glutamate at residue 75, a residue other than glutamate or serine at residue 81, e.g., a nonconservative substitution for glutamate at residue 81, a residue other than glutamate or serine at residue 82, e.g., a nonconservative substitution for glutamate at residue 82, and optionally a residue other than tryptophan or at residue 78, e.g., a nonconservative substitution at residue 78, of NS2 of influenza A virus, or any combination thereof. Conservative amino acid substitutions generally refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chains is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine. In contrast, nonconservative amino acid substitutions generally refer to dissimilar side chains or a differently charged residue, e.g., one which may result in a substitution of a polar for a nonpolar side chain or a nonpolar side chain for a polar side chain.

In one embodiment, the influenza virus of the invention includes one or more influenza virus proteins (polypeptides) having substantially the same amino acid sequence as one of SEQ ID NOs:1-7 (NS2) and optionally one of SEQ ID NOs:8-14 (NS1), so long as the NS2 protein does not have a glutamate residue at a residue corresponding to one or more of positions 67, 74, 75, 81 or 82 or corresponding to a tryptophan at position 78 and optionally does not have a glutamate residue at a residue corresponding to one or more of positions 67, 74, 75, 81 or 82. An amino acid sequence which is substantially the same as a reference sequence has at least 95%, e.g., 96%, 97%, 98% or 99%, amino acid sequence identity to that reference sequence, and may include sequences with deletions, insertions, and/or substitutions, e.g., those that result in a viral protein that is capable of being expressed at substantially the same level as the reference protein and optionally the same cellular location. In one embodiment, the one or more residues which are not identical to those in the reference sequence may be conservative or nonconservative substitutions which one or more substitutions do not substantially alter the expressed level of the protein with the substitution(s), and/or the level of virus obtained from a cell infected with a virus having that protein. As used herein, "substantially the same expressed level" includes a detectable protein level that is about 80%, 90% or more, the protein level of a full-length mature polypeptide, such as one corresponding to one of SEQ ID NOs:1-14. In one embodiment, the virus comprises a NS polypeptide with one or more, for instance, 2, 5, 10, 15, but no more than 20, amino acid substitutions, e.g., substitutions of up to 5% of the residues of the full-length, mature form of a polypeptide having SEQ ID NOs:1-14. The isolated virus of the invention may be employed alone or with one or more other virus isolates, e.g., other influenza virus isolates, in a vaccine, to raise virus-specific antisera, and/or in gene therapy. Accordingly, the invention provides host cells infected with the virus of the invention.

As also described herein below, it was found that NS2 alone, and the combination of NS2 and M1, inhibited viral polymerase activity. Both E67S/E74S and E67S/E74S/E75S mutants in the absence of M1 inhibited viral polymerase activity, similar to the inhibition observed with wild-type NS2. In the presence of M1, the E67S/E74S mutant inhibited viral polymerase to a greater extent than in the absence of M1 while the presence of M1 did not enhance the inhibition of viral polymerase activity by the E67S/E74S/E75S mutant. Therefore, residues E67/E74/E75 are likely important for the interaction between NS2 and M1 which in turn may modulate influenza virus polymerase activity.

The invention thus provides a method to identify an agent that modulates the interaction between NS2 and M1. The method includes contacting a cell with vectors encoding influenza virus PA, influenza virus PB1, influenza virus PB2, influenza virus NP, influenza virus M1 and influenza virus NS2, a vector for vRNA production having a reporter gene, and one or more agents. The expression of the reporter gene in the cell in the presence of the one or more agents is compared to the expression of the reporter gene in the absence of the vector encoding NS2 and/or the vector encoding M1 or to the expression of the reporter gene in the absence of the one or more agents. In one embodiment, the NS2 is a wild-type NS2, e.g., one having a glutamate residue at positions 67, 74 and 75. Further provided is a cell-free assay which employs isolated M1 protein and isolated NS2 protein to identify one or more agents that modulate the interaction between NS2 and M1.

Further provided is a method to identify a variant N2 protein that when expressed in influenza virus infected cells does not substantially alter the in vitro replication of the virus but is associated with attenuation of the virus in vivo. The method includes contacting a cell with vectors encoding influenza virus PA, influenza virus PB1, influenza virus PB2, influenza virus NP, influenza virus M1 and a variant influenza virus NS2 (one having one or more substitutions relative to a wild-type NS2) and a vector for vRNA production having a reporter gene. The expression of the reporter gene in the cell is compared to the expression of the reporter gene in a corresponding cell that expresses wild-type NS2. In one embodiment, reporter expression in the cell with the variant NS2 that is greater than that of the cell with the wild-type NS2 is indicative of a variant NS2 that may be associated with attenuation of influenza virus in vivo.

In one embodiment, the invention provides a method to identify a variant NS2 protein that alters the interaction between M1 and NS2. The method includes contacting a cell with vectors encoding influenza virus PA, influenza virus PB1, influenza virus PB2, influenza virus NP, influenza virus M1 and a variant influenza virus NS2, and a vector for vRNA production having a reporter gene. Then the expression of the reporter gene in the cell is compared to the expression of the reporter gene in a corresponding cell that expresses wild-type NS2. In one embodiment, reporter expression in the cell with the variant NS2 that is different than that of the cell with the wild-type NS2 is indicative of a variant NS2 with an altered interaction with M1.

Further provided is a method to prevent, inhibit or treat influenza virus infection or replication. The method includes administering to a vertebrate having or at risk of influenza virus infection an amount of isolated influenza virus NS2 protein and isolated influenza virus M1 protein, or of isolated nucleic acid encoding NS2 and isolated M1, effective to inhibit influenza virus polymerase.

Thus, the invention provides compounds for use in medical therapy, such as agents useful to inhibit influenza virus polymerase, optionally in conjunction with other compounds that prevent, inhibit or treat influenza virus infection. Also provided is the use of the compounds for the manufacture of a medicament to prevent, inhibit or treat influenza virus infection or replication, for example, by inhibiting influenza virus polymerase.

BRIEF DESCRIPTION OF THE FIGURES

FIG. 1. NS mutants used in this study (SEQ ID NOs:15-24). (A) The structure of NS2 reveals an amphipatic helical hairpin that dimerizes as a four-helix bundle. The W78 is surrounded by a patch of negative charges (E67, E74, E75, E81, and E82) and seems to be involved in the interaction between NS2/NEP and the NLS of M1 (Akarsu, 2003). (B) Point mutants created in NS2 are located in the M1-binding domain. The C-terminal sequence of NS1 is also shown.

FIG. 2. Subcellular localization of the NS2/NEP and NS1 proteins of the NS mutants. Virus-infected MDCK cells were fixed at 9 hours post-infection and the viral proteins visualised by indirect immunofluorescence. NS2 is visualised by staining with a polyclonal primary rabbit and an Alexa594-conjugated secondary antibody. NS1 is stained with a mouse monoclonal primary and an Alexa488-conjugated secondary antibody.

FIG. 3. Electron microscopy of the NS mutants. Viruses in the supernatants of infected MDCK cells were observed after negative staining. For thin-section observations, virus-infected cells were fixed at 12 hours post-infection and then processed for testing.

FIG. 4. Growth properties of the NS mutants in MDCK cells. The differences in intracellular expression and virion morphology observed among the mutants were not reflected in the overall growth of the viruses in MDCK cells FIG. 5. Virulence of the NS mutants in mice. Viruses were inoculated intranasally at a dose of $10^5$ PFU per mouse (n=4/group). Body weight was measured each day after inoculation. The wild-type virus killed 2 mice at day 9 (50% lethality), whereas none of the mutants killed any mice. Changes in body weight are shown.

FIG. 6. Immunization schedule.

FIG. 7. Survival ratio for immunized mice.

FIG. 8. Sequences of exemplary wild-type NS2 proteins (SEQ ID NOs:1-7) and wild-type NS1 proteins (SEQ ID NOs:8-14).

FIG. 9. Luciferase assay to detect viral polymerase activity in the presence of NS2 proteins or NS2 proteins and M1 protein.

FIG. 10. Virus growth kinetics for equine influenza viruses with NS mutations.

FIG. 11. Virus titers in the lungs of mice after infection with an equine influenza virus isolate (RG-Ohio), an equine influenza virus isolate (RG-Ohio) with a deletion of the 11 C-terminal residues of M2, and an equine influenza virus isolate (RG-Ohio) with NS mutations. No attenuation was observed for the equine viruses.

DETAILED DESCRIPTION OF THE INVENTION

Definitions

As used herein, the terms Aisolated and/or purified@ refer to in vitro preparation, isolation and/or purification of a vector, plasmid, protein (polypeptide), or virus of the invention, so that it is not associated with in vivo substances, or is substantially purified from in vitro substances. An isolated virus preparation of the invention is generally obtained by in vitro culture and propagation and is substantially free from other infectious agents. As used herein, Asubstantially free@ means below the level of detection for a particular infectious agent using standard detection methods for that agent. A Arecombinant@ virus is one which has been manipulated in vitro, e.g., using recombinant DNA techniques to introduce changes to the viral genome. For example, "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide (1) is not associated with proteins found in nature, (2) is free of at least one protein from the same source, e.g., free of at least one influenza virus protein, (3) is expressed by a cell from a different species, or (4) does not occur in nature. In contrast, non-isolated polypeptides (e.g., proteins and enzymes) are found in the state they exist in nature. The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome.

An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix (see Henikoff & Henikoff, 1989). See http://www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a gene segment with both NA and NB sequences. Influenza C virus has only seven gene segments.

Cell Lines That Can Be Used in the Present Invention

Any cell which supports efficient replication of influenza virus can be employed in the invention, including mutant cells which express reduced or decreased levels of one or more sialic acids which are receptors for influenza virus. Viruses obtained by the methods can be made into a reassortant virus.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The virus may be purified by a process that has been shown to give consistent results, before vaccine production (see, e.g., World Health Organization, 1982).

A complete characterization of the cell lines to be used is conducted so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

The virus produced in the cell may be highly purified prior to vaccine or gene therapy formulation. Generally, the purification procedures will result in the extensive removal of cellular DNA, other cellular components, and adventitious agents. Procedures that extensively degrade or denature DNA can also be used.

Any cell, e.g., any avian or mammalian cell, such as a human, canine, bovine, equine, feline, swine, ovine, mink, e.g., MvLu1 cells, or non-human primate cell, including mutant cells, which supports efficient replication of influenza virus can be employed to isolate and/or propagate influenza viruses. Isolated viruses can be used to prepare a reassortant virus, e.g., an attenuated virus. In one embodiment, host cells for vaccine production are those found in avian eggs. In another embodiment, host cells for vaccine production are continuous mammalian or avian cell lines or cell strains.

Influenza Vaccines

A vaccine of the invention includes an isolated attenuated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the attenuated virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including an attenuated recombinant virus of the invention can be used for preventing or treating influenza virus infection. For attenuated viruses other than the attenuated recombinant virus of the invention, or to further attenuate the virus of the invention, attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens must come from the reassorted viruses or clinical isolates. The attenuated genes are derived from the attenuated parent. In this approach, genes that confer attenuation preferably do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 µg, e.g., 30 to 100 µg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-$\alpha$, interferon-$\beta$, interferon-$\gamma$, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, an attenuated viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, an attenuated vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus isolate of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU)/kg, or any range or value therein. The dose of inactivated vaccine may range from about 0.1 to 1000, e.g., 30 to 100 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Heath Service (PHS), which is usually 15 μg, per component for older children. 3 years of age, and 7.5 μg per component for older children<3 years of age. The quantity of NA can also be standardized, however, this glycoprotein can be labile during the processor purification and storage (Kendal et al., 1980; Kerr et al., 1975). Each 0.5-ml dose of vaccine may contains approximately 1-50 billion virus particles, and preferably 10 billion particles.

The invention will be further described by the following non-limiting examples.

EXAMPLE 1

Materials and Methods

Cells. 293T human embryonic kidney cells and Madin-Darby canine kidney (MDCK) cells were maintained in Dulbecco's modified Eagle's medium supplemented with 10% fetal calf serum and in minimal essential medium (MEM) containing 5% newborn calf serum, respectively. The 293T cell line is a derivative of the 293 cell line into which the gene for the simian virus 40 T antigen was inserted. All cells were maintained at 37° C. in 5% $CO_2$.

Construction of plasmids. Genes of the A/WSN/33(H1N1) virus were cloned into the pPolI vector described in Neumann et al. (1999). Briefly, vRNAs were reverse-transcribed, the corresponding cDNAs were amplified with a BsmBI site at their 5' end and cloned into a pPolI plasmid containing the human RNA polymerase I promoter and the mouse RNA polymerase I terminator separated by BsmBI sites. The NS2/NEP mutant genes used in the experiments were constructed by PCR using back-to-back primers, 5'-gagagacgtctcgaaataagaagcttgattgaagaagtga gacacaaact-gaagataacagag-3' (SEQ ID NO:25) and 5'-gagagacgtctc-tatttcttcaaacttctgacctaattgttcccgc-3' (SEQ ID NO:26) for the mut-W78; 5'-gagagacgtctectgacctaattgcgaccgccattt tccgtttctgattggagtgagtgg-3' (SEQ ID NO:27) and 5'-gagagacgtctcggtcagaagttttcggaaataagatggtt gattgaaga agtgagacacagactg-3' (SEQ ID NO:28) for the mut-E67/E74/tail; and 5'-gagagacgtctcctgacctaattgcgac-cgccattttccgtttctgttttggagtgagtgg-3' (SEQ ID NO:29) and 5'-gagagacgtcteggtcagaagttttcgtcgataagat ggttgattgaa-gaagtgagacacagactg-3' (SEQ ID NO:30) for the mut-E67/E74/E75/tail. These primers have a BsmBI site at their 5' ends. The PCR products were isolated with a reaction clean-up kit (Qiagen), digested with BsmBI and DpnI (Biolabs) and then transformed into *Escherichia coli* strain DH5α for amplification. All constructs were subsequently sequenced to verify the mutations.

Plasmid-based reverse genetics. In all experiments, A/WSN/33 genes were used to produce the viruses, except for the M gene, which was derived from the A/Puerto Rico/8/34 (PR8; H1N1) strain. Briefly, recombinant viruses were generated using eight plasmids expressing all viral RNAs, and four plasmids expressing the viral nucleoprotein (NP) and the three subunits of the viral polymerase PB1, PB2 and PA (Neumann et al., 1999). Transfectant viruses were collected approximately 48 hours post-infection (h.p.i.) and stored as viral stocks for use in subsequent experiments. Virus titers were determined by 10-fold serial dilutions of supernatant by a standard plaque assay on MDCK cells in triplicate for each dilution and are given in plaque forming units (PFU).

Immunofluorescence staining. MDCK cells were infected with recombinant viruses at a multiplicity of infection (MOI) of 5 PFU per cell. At 9 h.p.i., the cells were fixed with 4% paraformaldehyde and permeabilized with 0.5% Triton X-100. The cells were then incubated with the primary antibodies specific to the viral proteins. The anti-NS2 antibody was a rabbit polyclonal (laboratory clone R5023) raised against recombinant NS2; the anti-NP antibody was a mouse monoclonal (laboratory clone 68D2) raised against viral NP; the anti-M1 antibody was a mouse monoclonal (laboratory clone 174/4) raised against viral M1; the anti-NS1 antibody was a mouse monoclonal (laboratory clone P601) raised against the recombinant protein. After 3 washes with phosphate buffered-saline (PBS), the cells were incubated with a goat polyclonal secondary antibody coupled with Alexa488 to the anti-mouse and Alexa594 to the anti-rabbit IgGs (Molecular Probes), and washed 3 times. The sub-cellular localizations of the different viral proteins were visualized with an epifluorescent UV microscope (Nikon).

Electron microscopy. For thin-section electron microscopy, MDCK cells were infected with virus at an MOI of 5 PFU/cell and incubated in MEM with TPCK-trypsin (1 µg/mL) at 37° C. At 12 h.p.i., the MDCK cells were washed with PBS, prefixed with 2.5% glutaraldehyde in 0.1 M cacodylate buffer (pH 7.4) for 1 hour at 4° C., and then fixed with 2% osmium tetroxide in the same buffer for 1 hour at 4° C. Specimens were subsequently stained en bloc with 1% aqueous uranyl acetate for 30 minutes at 4° C. and processed as described in Noda et al. (2006). For negative staining, the culture medium from the MDCK cells infected with wild-type or mutant viruses was collected at 24 h.p.i. onto a Formvar-coated copper grid, stained with 2% phosphotungstic acid solution, and examined with a Hitachi H-7500 electron microscope at 80 kV.

Viral pathogenicity in mice. Four-week-old female BALB/c mice (n=4/group) were infected intranasally with 50 µL of viral suspension containing $10^5$ PFU of a recombinant virus in sterile 0.9% sodium chloride. Animals were monitored daily for survival or changes in body weight over the next 2 weeks.

Vaccine studies. At day 0, four-week-old female BALB/c mice (n=12) were infected intranasally with the mutant virus (mut-E67/E74/tail). As a control, mice (n=11) were inoculated with PBS. At day 25 post-vaccination (challenge day), all of the mice were similarly infected with 10 median mouse lethal doses ($MLD_{50}$) of wild-type virus A/WSN/33. Survival was recorded daily for the next 14 days post-challenge. On days 3 and 6 post-challenge, 3 mice were euthanized and their lungs were harvested and titrated for the presence of virus.

Results

Previously the three-dimensional structure of the M1-binding domain of NS2/NEP was determined. A tryptophan residue (W78) surrounded by a cluster of glutamate residues (E67, E74, E75, E81 and E82), forming a negatively charged patch, was found to be a major M1-binding epitope for this protein (Akarsu et al., 2003). Pull-down experiments have shown that the W78 of NS2/NEP is a critical binding center for the basic nuclear localization signal (NLS) motif $^{101}$RKLKR$^{105}$ in the N-terminal fragment of M1 (Baudin et al., 2001; Sha and Luo, 1997) via its support of electrostatic interactions with the surrounding acidic glutamate residues.

To further characterize NS2/NEP, a series of NS2/NEP mutants for W78 or the glutamate residues was generated using reverse genetics and assessed for phenotypic changes in virus replication. Because of the overlap of the E67 and E74 residues of the NS2/NEP with the C-terminal region of NS1, mutations at the glutamate residues cause NS1 to gain mutations or insertions of additional residues to its C-terminus. The effect, if any, of these alterations in NS1 is discussed below, as is the role of NS2/NEP in influenza virus morphogenesis and pathogenesis.

Generation of NS mutants. Based on the crystal structure of the C-terminal M1-binding domain of NS2/NEP (Akarsu et al., 2003), reverse genetics was used to generate a W78S mutant, as well as a series of glutamate mutants including single (E75S), double (E67S/E74S) or triple (E67S/E74S/E75S) mutations, to assess for phenotypic changes in virus replication (FIG. 1). All of these residues are highly conserved among the NS2 proteins of the influenza A strains, and residues E67, E74, and E75 are also found in influenza B viruses. Notably, due to gene overlap, the NS2/NEP E67S mutation caused G224V/T225A mutations in NS1 and the NS2/NEP E74S mutation suppressed the stop codon for NS1, resulting in the addition of seven residues (termed the "tail" herein, residues 231-237) to the C-terminus of NS1 (FIG. 1). The mutant viruses were designated mut-W78, -E75, -E67/E74/tail, or -E67/E74/E75/tail, respectively.

Intracellular localization of the NS mutant proteins. The expression and stability of each mutant was tested by using an immunofluorescence assay. In mut-W78 (FIG. 2) and mut-E75 (data not shown)-infected cells, NS1 was mostly found in the cytoplasm but also inside the nucleolus as bright spots similar to those seen in wild-type virus-infected cells, supporting the expression of the intact NS1 protein in these two viruses. NS2/NEP of mut-W78 was present in small amounts in the cytoplasm but was more concentrated in the nucleus, where it was strictly excluded from the nucleolus, as was that of the wild-type virus. Similarly, the localization of mut-E67/E74/tail NS1 was equivalent to that of the wild-type virus, indicating that the additional tail sequence did not affect NS1 expression (FIG. 2). By contrast, NS1 of the mut-E67/E74/E75/tail showed a dramatic change in subcellular distribution, as it concentrated in the nucleoplasm only and was absent from the cytoplasm, indicating that the sequence difference between the additional NS1 tails of mut-E67/E74/tail and mut-E67/E74/E75/tail rendered different intracellular localization of these NS1 mutants. NS2/NEP expression and localization of all of the mutants was equivalent to that of the wild-type virus, except for mut-E67/E74/E75/tail, whose NS2/NEP expression levels were decreased drastically compared to that of the wild-type virus.

Figure 3:
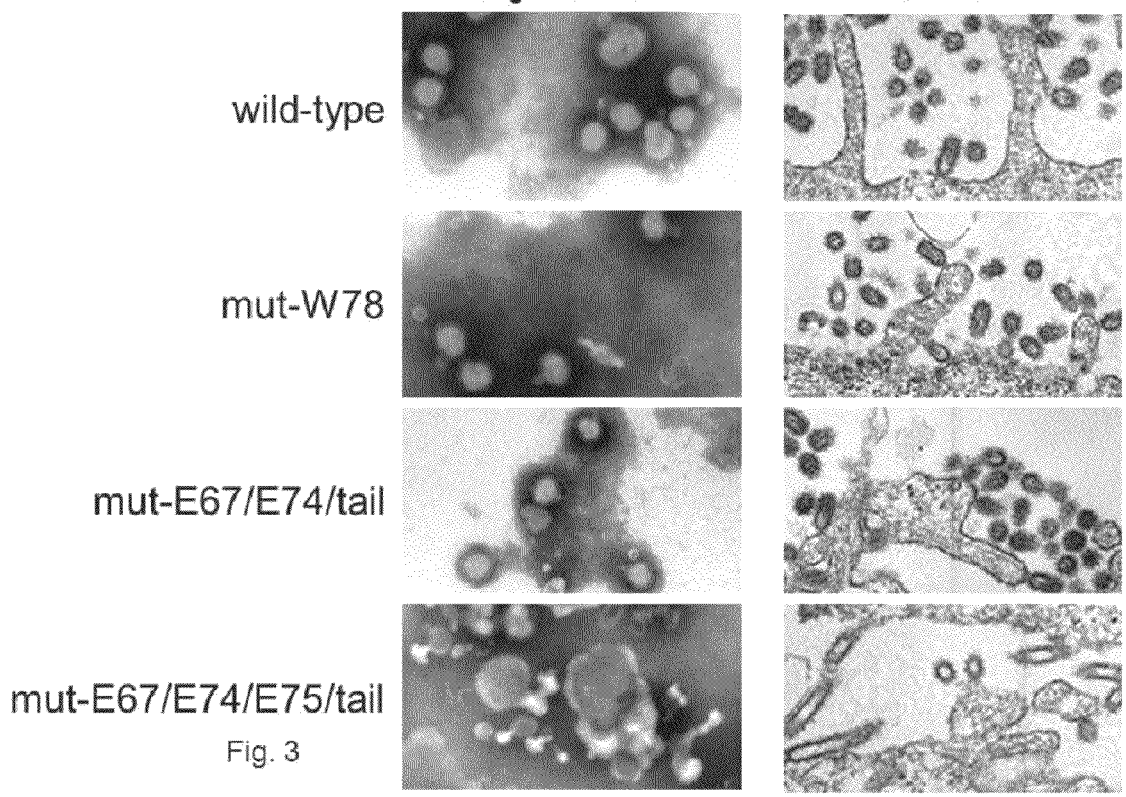
Figure 4:
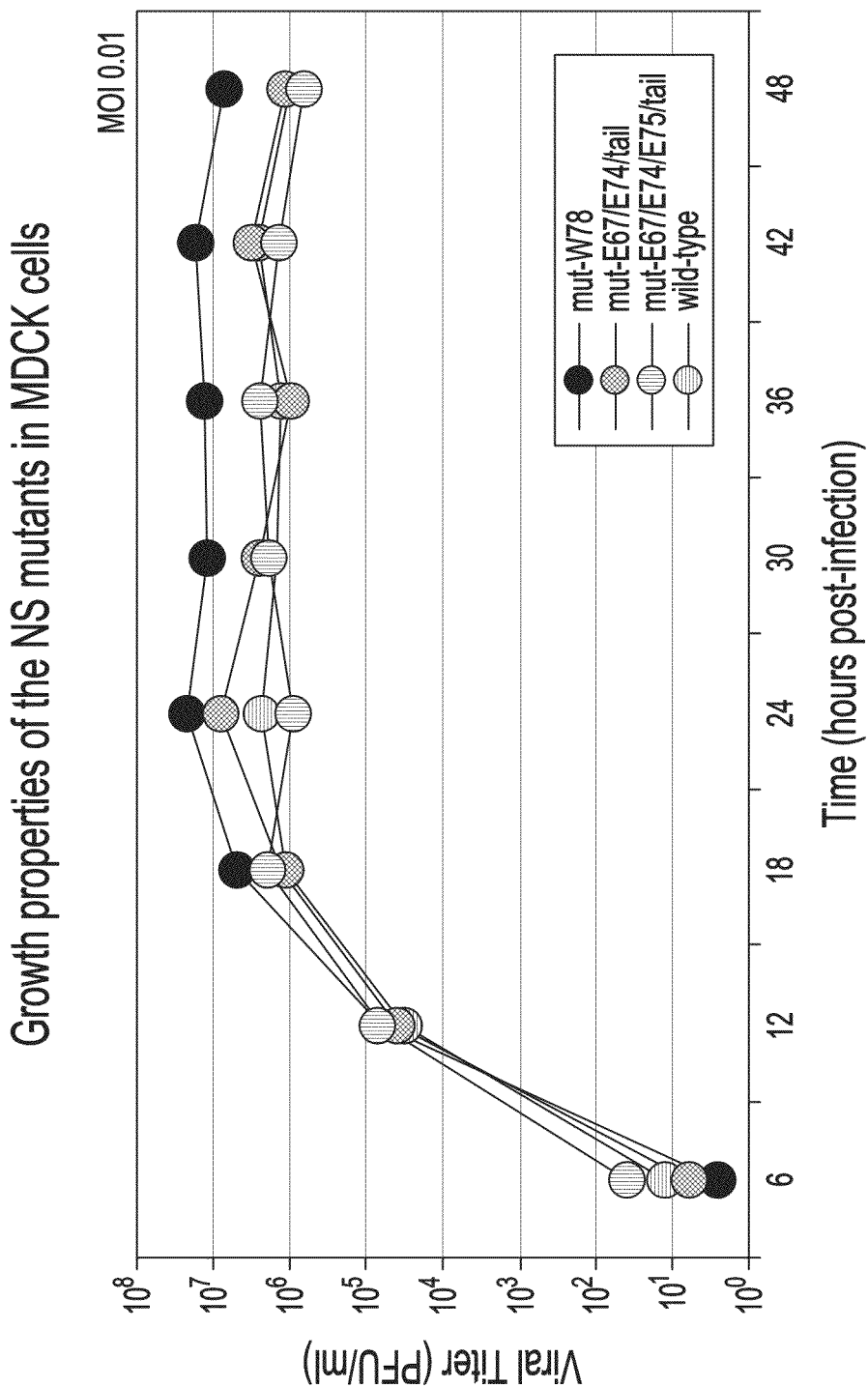

Morphology of the NS mutants by electron microscopy. The wild-type virus formed mainly spherical virions of 80-120 nm in diameter, as shown by negative staining (FIG. 3). The mut-W78 and mut-E67/E74/tail showed similar morphology to that of the wild-type. By contrast, the mut-E67/E74/E75/tail exhibited a dramatic change in morphology with a high degree of pleiomorphism. Moreover, compared to the wild-type and other mutants, the thin sections of the mut-E67/E74/E75/tail-infected cells showed elongated virus particles and revealed a large population of "empty" particles that appeared to lack any ribonucleoprotein complexes (FIG. 3). These results suggest that the cluster of glutamate residues on the M1-binding domain of NS2/NEP plays an important role in spherical virion formation.

Growth properties in cell culture of the NS mutants. The growth properties of the mutants were compared with that of wild-type virus in MDCK cells. Each virus was infected at an MOI of 0.01, and growth kinetics was monitored. Surprisingly, no significant differences were found between the growth rates of the mutants and the wild-type virus (data not shown), indicating that the differences in intracellular expression (FIG. 2) and in virion morphology (FIG. 3) observed among the mutants were not reflected in the overall growth of the viruses in this cell line.

Figure 5:
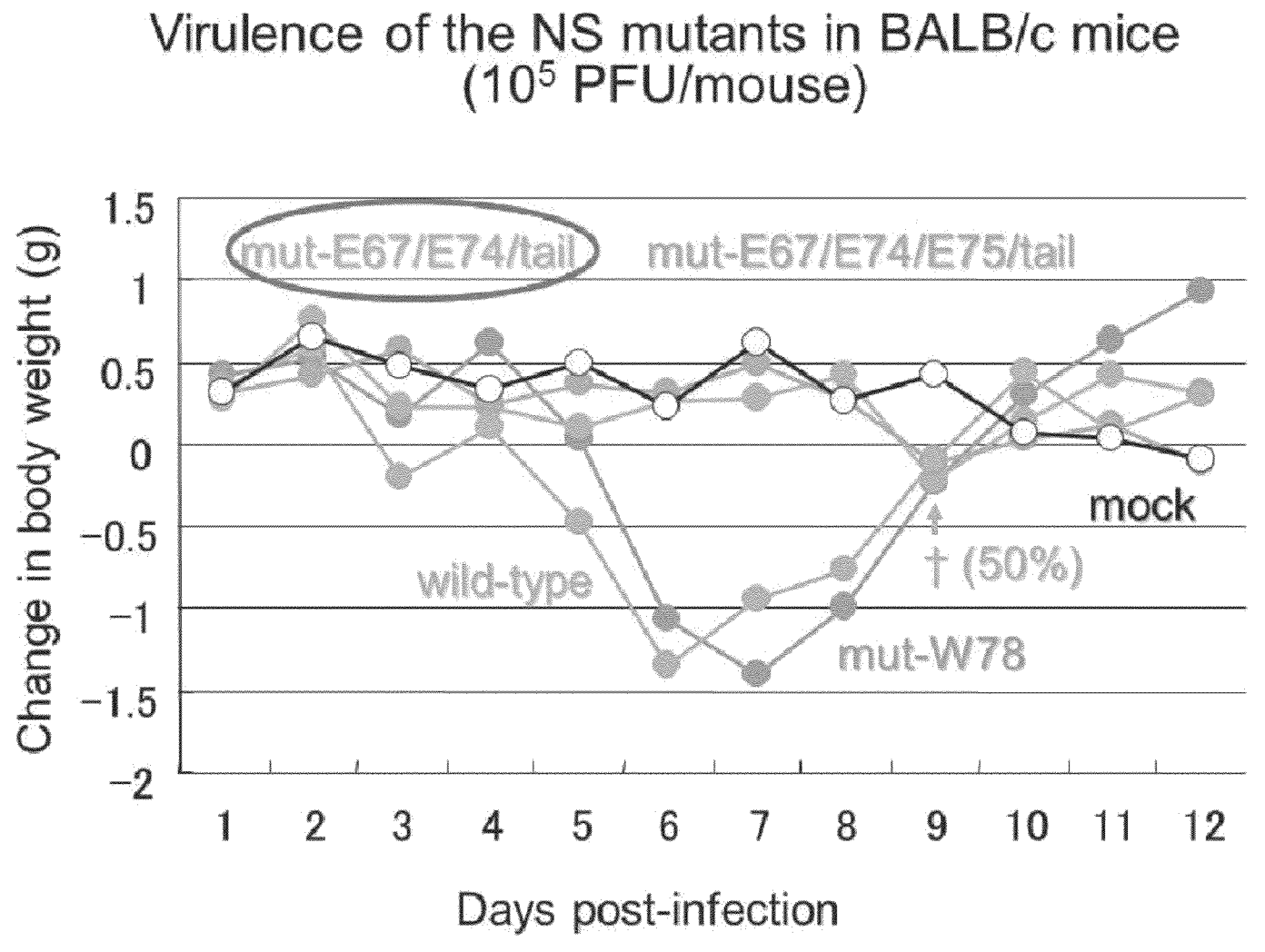

Virulence in mice of the NS mutants. The pathogenicity in mice of the mutants was tested as an indicator of in vivo virus growth. Mut-E67/E74/tail and mut-E67/E74/E75/tail caused no weight loss in mice after intranasal infection with $10^5$ PFU, unlike the wild-type virus, which caused 50% of the mice to die by day 9 post-inoculation, indicating an attenuated phenotype of these mutants in this animal (FIG. 5). By contrast, the mut-W78 induced weight loss in mice but no deaths as the diseased mice recovered, indicating that this mutant also exhibited an attenuated phenotype, albeit to a lesser extent than the other mutants.

Potential of an NS mutant as a live vaccine. As a live vaccine, viruses must replicate to high titers and must be attenuated. At least the mut-E67/E74 virus appears to fulfill these criteria. Next, the immunogenicity of this virus was tested in a mouse model. Intranasally, mice were immunized with mut-E67/E74 and 25 days after immunization, challenged with 10 $LD_{50}$ of wild-type WSN virus. All immunized mice survived upon lethal WSN challenge and no virus was recovered from the lungs of the challenged mice, unlike the controls (Table 1). These results demonstrate that this NS mutant has potential as a live vaccine.

TABLE 1

Protective immunity of the NS mutant to lethal challenge with virulent virus

| Virus | Virus titer in lung ($\log_{10}$PFU/g) | | Lethality (dead no./ total no.) |
|---|---|---|---|
| | Day 3 | Day 6 | |
| mut-E67/E74/tail | <2.5, <2.5, <2.5 | <2.5, <2.5, <2.5 | 0/11 (0%) |
| mock (PBS) | 7.18, 7.25, 7.36 | 3.70, 4.81, 5.41 | 11/11 (100%) |

Virus titers in lungs were determined from 3 mice per group; individual titers are shown (n = 3). Detection limit is $10^{2.5}$ PFU/g.
Lethality was determined at 14 days post-challenge with wild-type WSN virus (10 $MLD_{50}$).

Discussion

Previously, it was found that the tryptophan (W78) residue surrounded by a cluster of glutamate residues in the C-terminal region of the NS2/NEP protein of influenza A virus, was important for binding to the N-terminal region of M1 (Akarsu et al., 2003). In the present study, a series of NS2/NEP mutants was generated for W78 and three glutamate residues (E67, E74, and E75) conserved among influenza A and B viruses and the functional responsibility of these residues to the interaction between M1 and NS2/NEP in virus replication was assessed in vitro and in vivo. The results strongly suggest that these residues are responsible in concert for efficient virus growth in mice, but are not critical for growth in cell culture, an important attribute for attenuating mutations in live vaccines.

Amino acid substitutions E67S or E74S in NS2/NEP accompanied G224V/T225A mutations or disruption of the stop codon by adding seven amino acid residues ($^{231}$FGNKMVD$^{237}$; SEQ ID NO:31) to NS1, due to gene overlapping. It is likely that the additional amino acids to the C-terminus of NS1 alter NS1 function, since this region contains the PABII-binding domain (Chen et al., 1999) and a possible PDZ element (Obenauer et al., 2006), although several natural isolates, such as A/Udorn/72 (H3N2), possess NS1s of extended length (237 amino acids in total compared to 230 in WSN NS1), which are the same size as those of the mutants containing E74S. Here, it was shown that the mut-E67/E74/tail possessed similar virion morphology and growth kinetics to those of the wild-type virus in MDCK cells, indicating that NS1 mutants containing an artificially extended tail do not affect virus replication in this cell line. However, the intracellular localization of the mut-E67/E74/E75/tail NS1 was clearly different from that of the mut-E67/E74/tail NS1, suggesting that the sequence difference between these NS1 terminal tails could alter the behaviour of each NS1 protein in cells. A recent study indicated that a C-terminal extended tail containing two arginines at positions 231 and 232 of NS1 (e.g., Udorn strain) contributes to formation of the second nuclear localization signal (NLS2) which also functions as a nucleolar localization signal (NoLS) (Melen et al., 2007). There is a difference in total charge at this extended region of NS1 between mut-E67/E74/E75/tail ($^{231}$FVDKMVD$^{237}$; SEQ ID NO:32) and mut-E67/E74/tail ($^{231}$FGNKMVD$^{237}$; SEQ ID NO:31), raising the possibility that the different localization observed between the two NS1s may be explained by this property, without any significant difference in overall growth of the viruses in MDCK cells.

Previous studies showed that the two kinds of NS1 lengths, 230 amino acids (like the WSN strain) and 237 amino acids (like the Udorn strain), were evident among human influenza viruses, whereas the NS1s of avian-origin viruses are consistently 230 amino acids (with the exception of a couple of strains, such as A/turkey/Oregon/71 (H7N3) and A/Vietnam/1203/2004 (H5N1)), suggesting the possible presence of host-specific selection pressure (Suarez and Perdue, 1998). This idea may be supported by the present results showing that mutants with NS1s containing extended tails were attenuated in mice, although the precise molecular mechanism for the attenuation is unknown due to the presence of the concomitant NS2 mutations.

Simultaneous mutations at three glutamate residues (mut-E67/E74/E75/tail) of NS2/NEP resulted in a dramatic change in virion shape, showing pleiomorphism as well as a decrease in the ribonucleoprotein complex content inside virus particles; this was not apparent with mut-W78 and mut-E67/E74/tail. These results establish, for the first time, that the NS2/NEP influences viral particle shape and is involved in the assembly/incorporation of the genomic segments. Such morphological changes look similar to those that occur in viruses mutated in their M1 protein at its NLS (Burleight et al., 2005) and those mutated in the cytoplasmic tails of their HA, NA (Jin et al., 1997), or M2 (Iwalsuki-Horimoto et al., 2004). It has been shown that i) NS2/NEP, but not NS1, is present with several molecules in a viral particle (Richardson and Akkina, 1991), ii) NS2/NEP interacts directly with the NLS motif of M1 (Akarsu et al., 2003), and iii) M1 binds not only to the lipids (Baudin et al., 2001; Ruigrok and Baudin, 1995), thus possibly covering the inside surface of the viral envelope, but also to the viral glycoproteins HA and NA (Ali et al., 2000; Enami and Enami, 1996) and the vRNPs (Watanabe et al., 1996; Ye et al., 1999) through its C-terminal region (Akarsu et al., 2003; Baudin et al., 2001). The present observations, together with these findings, may lead to a hypothesis for virion assembly in that the complex of nuclear M1 (ncM1) and NS2/NEP with the vRNPs is translocated to the cytoplasm and goes to the plasma membrane covered by the cytoplasmic M1 (cyM1), which interacts with the HA, NA, and M2 cytoplasmic tails, resulting in binding to cyM1 via an ncM1/cyM1 interaction by M1 self-polymerization (Baudin et al., 2001). Thus, any decreased interaction between ncM1 and NS2/NEP as a result of a mutation(s) may alter virion morphology.

Here, it was found that mut-W78 showed an attenuated, albeit slightly, phenotype compared to the wild-type virus, indicating at least a partial role for the W78 of NS2/NEP in viral replication in mice, and confirming in vitro results (Akarsu et al., 2003). By contrast, the NS2/NEP mutants with double and triple glutamate substitutions showed a strikingly attenuated phenotype in mice, possibly suggesting weaker binding of these mutated NS2/NEPs to ncM1. In addition, as discussed above, the possibility that mutations in NS1 are responsible for the attenuated phenotype in mice of these mutants cannot be ruled out; the extended tail of NS1 with mut-E67/E74/tail and mut-E67/E74/E75/tail may mask the C-terminal cis-acting motifs, such as PABII-binding and PDZ domains, that may indirectly affect the functional transport of the ncM1/NS2/vRNP complex in mice but not in cell culture.

The present study demonstrated that the mutations introduced into mut-E67/E74/tail can be used to attenuate influenza viruses for use as live vaccines. Since mut-E67/E74/tail replicated as well as the wild-type virus, such viruses may serve as cell culture-based live influenza vaccines, negating issues of antigenic alteration caused by propagation of seed viruses in embryonated chicken eggs (Robertson, 1993). Thus, the use of NS mutants can be considered an option for the development of live vaccines against influenza.

EXAMPLE 2

Amino acids around W78 are important for inhibition of influenza viral polymerase activity M1 and NS2 are known inhibitors of influenza polymerase; however, their mechanism of inhibition has not been elucidated. Previously, the three-dimensional structure of the M1-binding domain of NS2 was determined and it was found that a tryptophan residue (W78) surrounded by a cluster of glutamate residues (E67, E74, E75, E81 and E82) that form a negatively charged patch is the major M1-binding epitope for this protein (Akarsu et al., 2003). Pull-down experiments showed that W78 is also a critical binding center for the nuclear localization signal (NLS) motif [101]RKLKR[105] (SEQ ID NO:33) in the N-terminal fragment of M1, via its support of electrostatic interactions with the surrounding glutamate residues. To further characterize NS2, reverse genetics was used to generate a series of NS2 mutants in which the glutamate residues were replaced (see Example 1).

Figure 6:
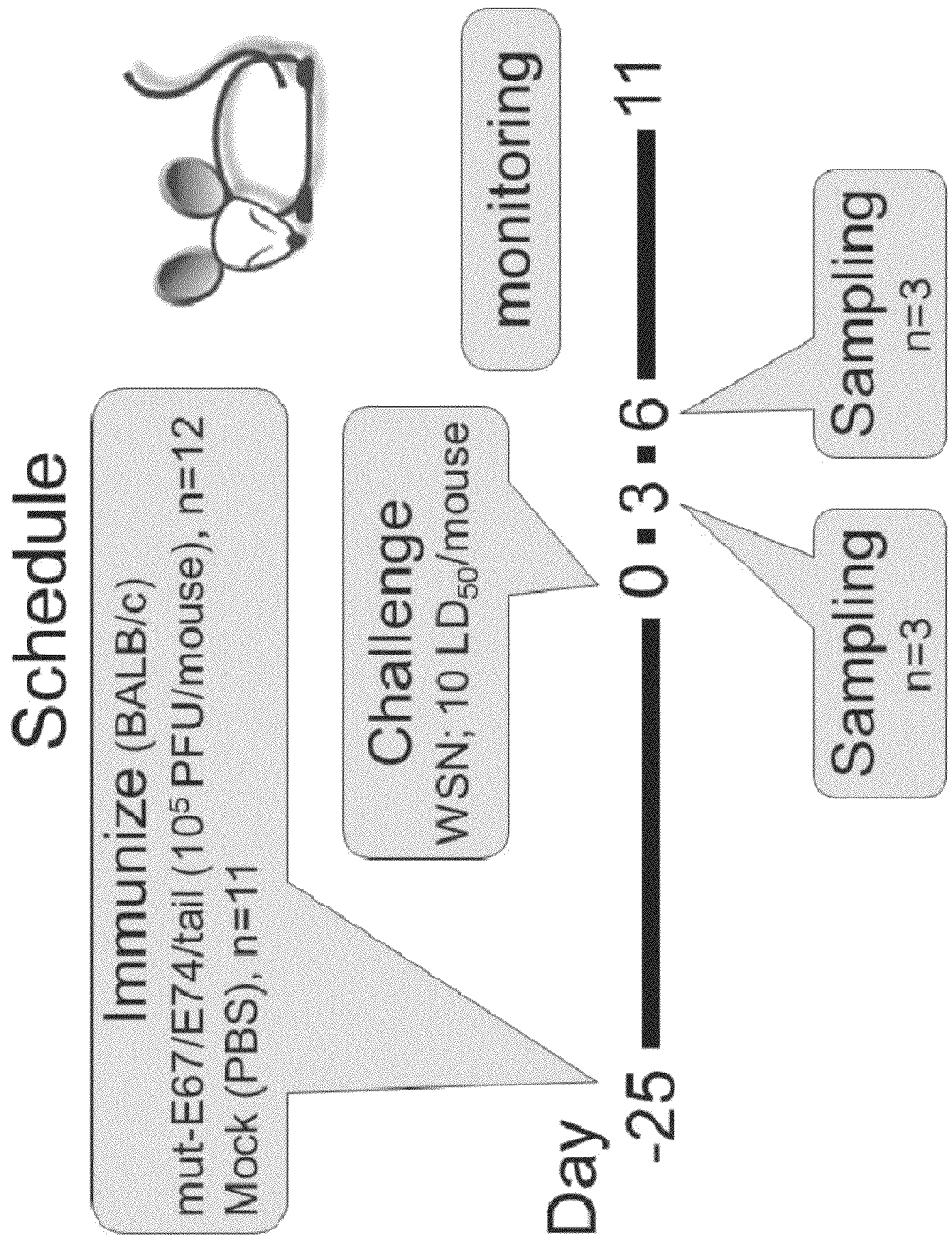
Figure 7:
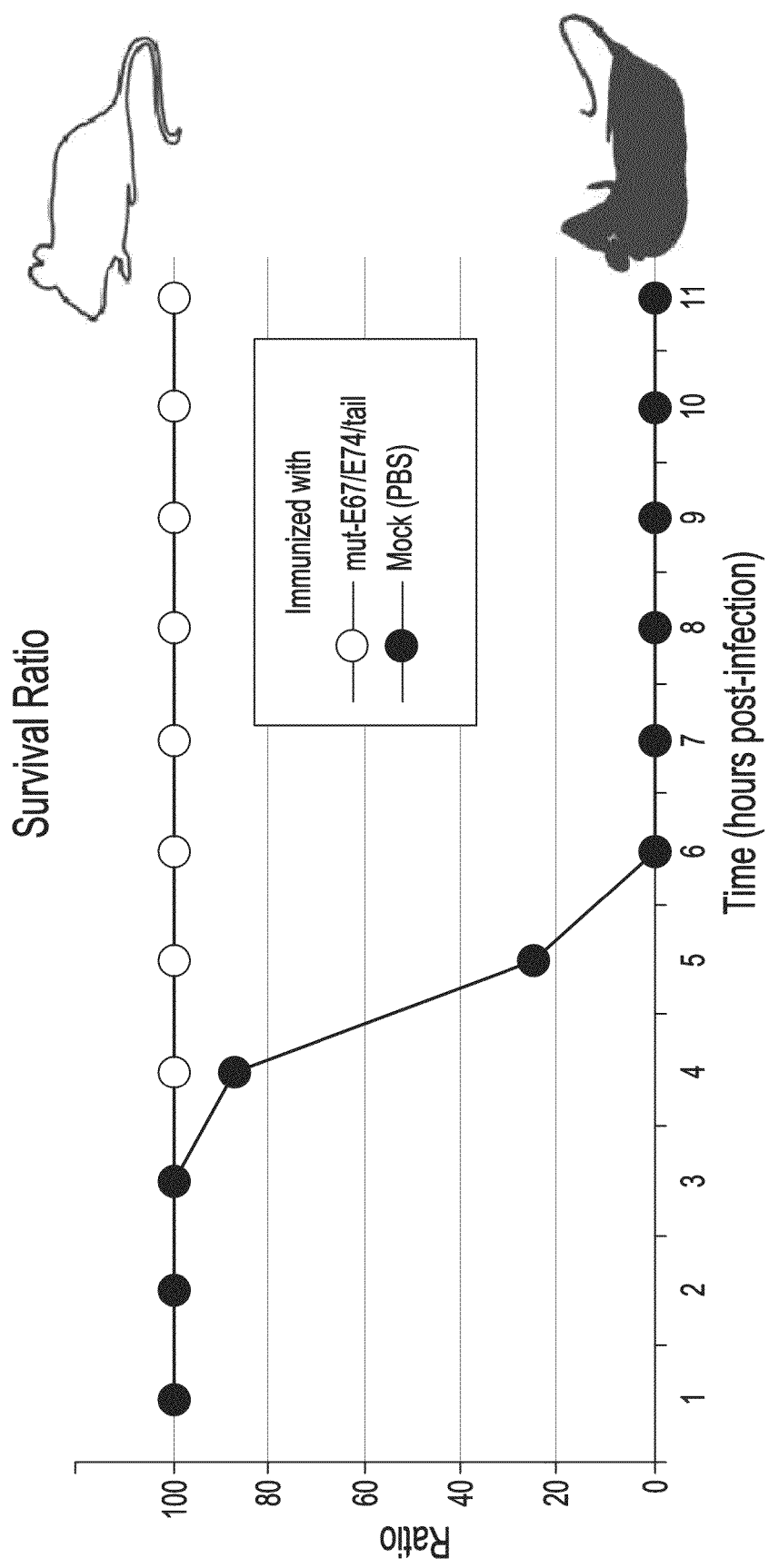
Figure 9:
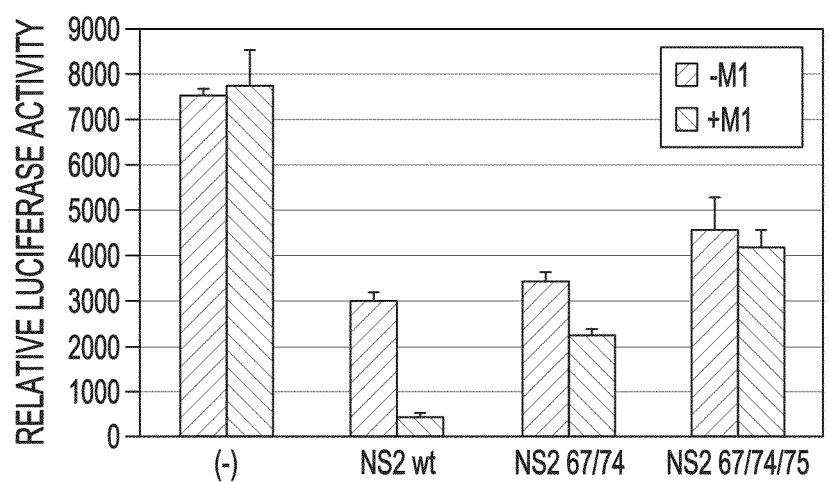
Figure 10:
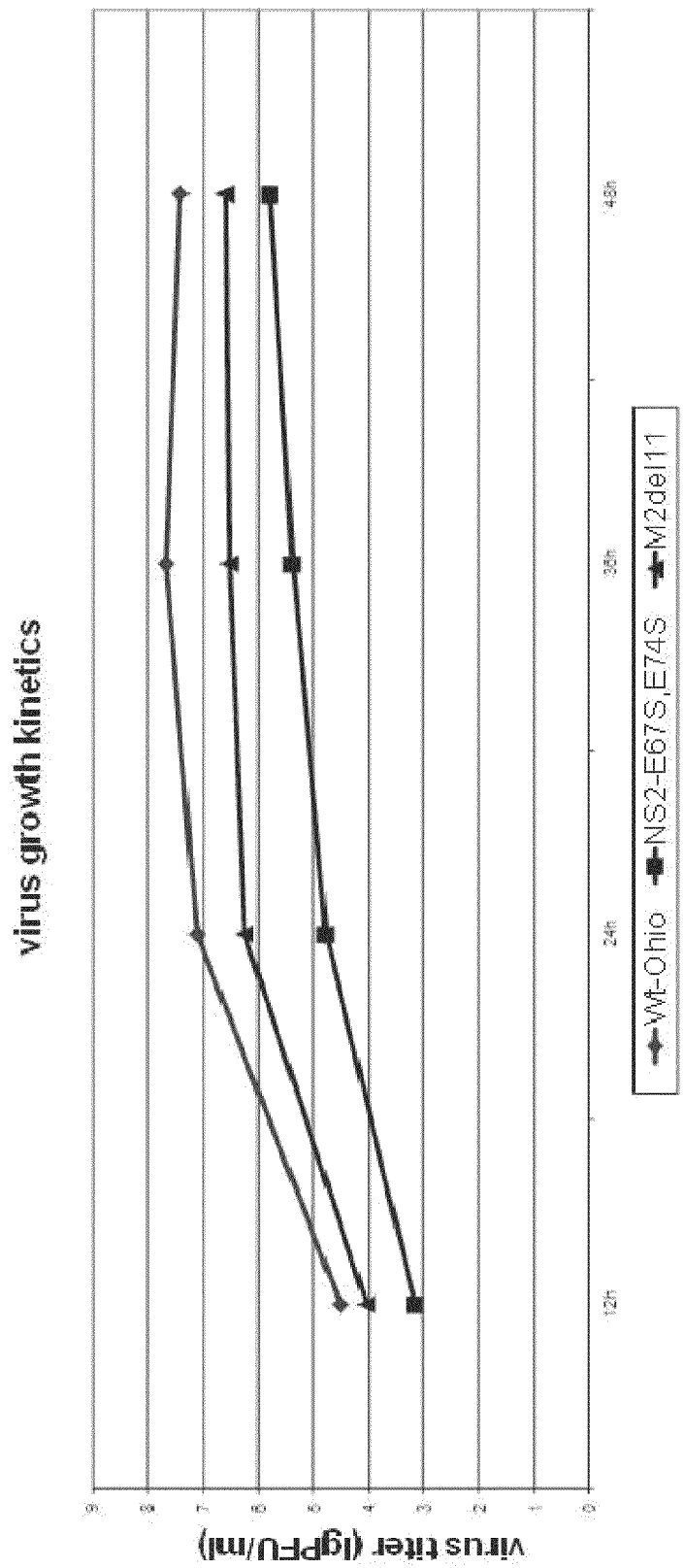
Figure 11:
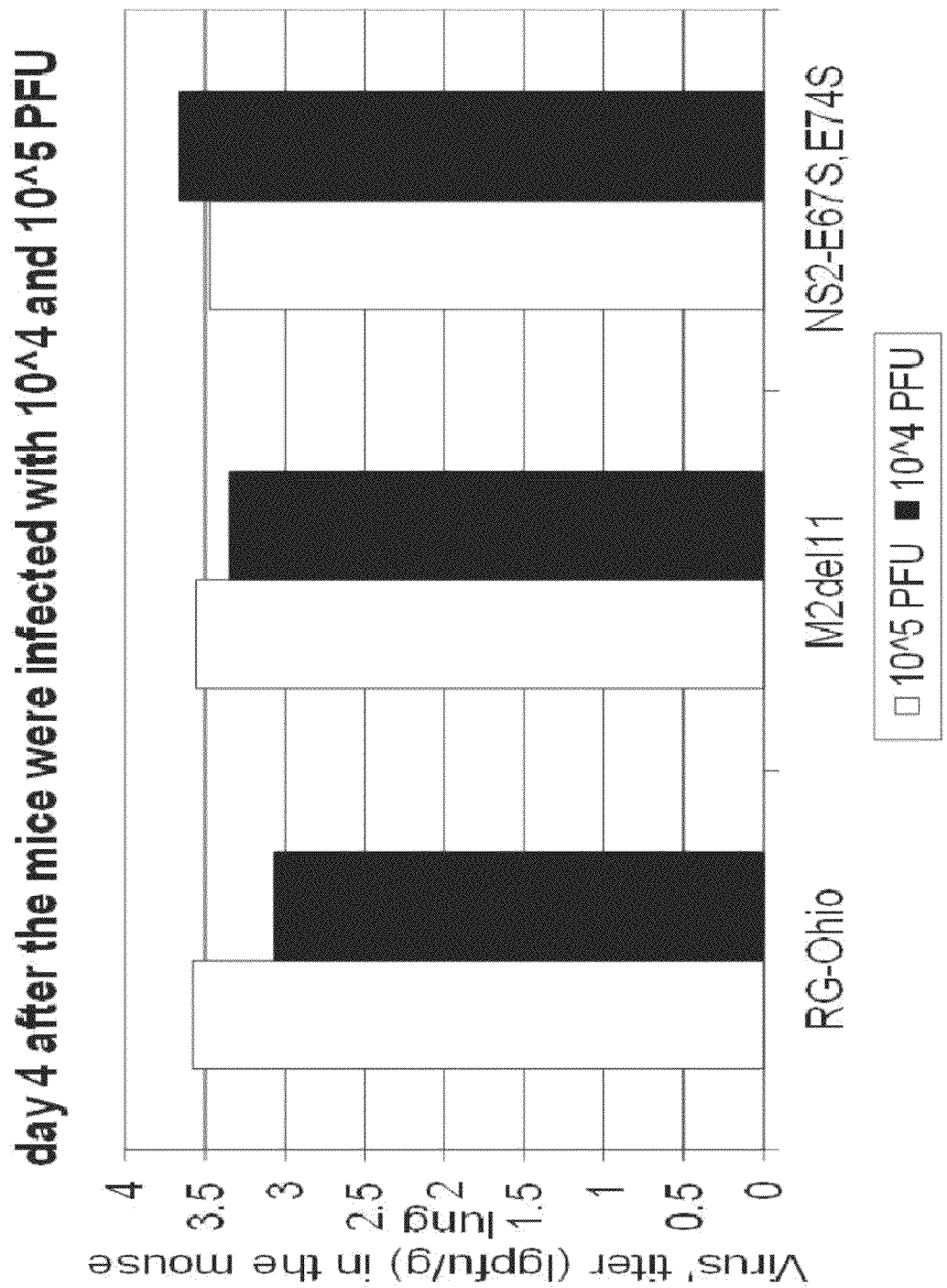

A luciferase assay was employed to evaluate the influenza viral polymerase activity in the presence of the NS2 mutants. Cells were transfected with 4 viral protein encoding vectors (encoding PA, PB1, PB2 and NP) and a PolI vector that expresses luciferase vRNA, as well as NS2 and/or M1 encoding vectors. Inhibition was observed when NS2 was expressed in the absence of M1, and further inhibition occurred when M1 was expressed in conjunction with NS2 in the assay (FIG. 6). This finding indicates that M1 and NS2 work together to inhibit viral polymerase activity. Using the NS2 mutants E67S/E74S and E67S/E74S/E75S, inhibition by the variant NS2 proteins in the absence of M1 expression was observed at a level similar to that of wild-type NS2. When M1 was expressed along with the variant NS2 proteins, some additional inhibition was observed with the E67S/E74S mutant, but almost no inhibition was observed with the E67S/E74S/E75S mutant (FIG. 6).

These results indicate that residues E67/E74/E75 are important for the interaction of NS2 with M1 and for the inhibition of influenza viral polymerase activity, and so may be a target in screening assays for agents useful to alter viral infection and/or replication, e.g., an agent that mimics M1 or NS2 in its interaction with NS2 or M1, respectively, thereby inhibiting the influenza virus polymerase. In addition, the altered interaction between the NS2 mutants and M1 may explain the attenuated phenotype observed with influenza viruses having the mutant NS2 protein. Further, because NS2 (wild-type or mutant), or NS2 and M1 together, inhibit the viral polymerase, they or nucleic acid encoding NS2 and/or M1, may be employed as an anti-viral.

References

Akarsu et al., *EMBO J.*, 22:4646 (2003).
All et al., *J. Virol.*, 74:8709 (2000).
Aragon et al., *Mol. Cell Biol.*, 20:6259 (2000).
Arzt et al., *Virology*, 279:439 (2001).
Baudin et al., *Virology*, 281:102 (2001).
Bergmann et al., *J. Virol.*, 74:6203 (2000).
Boulo et al., *Virus Res.*, 124:12 (2007).
Bui et al., *J. Virol.*, 74:1781 (2000).
Bullido et al., *J. Virol.*, 75:4912 (2001).
Burgui et al., *J. Gen. Virol.*, 84:3263 (2003).
Burleigh et al., *J. Virol.*, 79:1262 (2005).
Chen et al., *EMBO J.*, 18:2273 (1999).
de la Luna et al., *J. Virol.*, 69:2427 (1995).
Elton et al., *J. Virol.*, 75:408 (2001).
Enami et al., *J. Virol.*, 68:1432 (1994).
Enami and Enami, *J. Virol.*, 70:6653 (1996).

Fortes et al., *EMBO J.*, 13:704 (1994).
Greenspan et al., *J. Virol.*, 54:833 (1985).
Hatada et al., *J. Virol.*, 73:2425 (1999).
Inglis et al., *Proc. Natl. Acad. Sci. USA*, 76:3790 (1979).
Iwatsuki-Horimoto et al., *J. Virol.*, 78:10149 (2004).
Jin et al., *EMBO J.*, 16:1236 (1997).
Kim et al., *Proc. Natl. Acad. Sci. USA*, 99:10096 (2002).
Krug et al., *Virology*, 309:181 (2003).
Lamb and Choppin, *Annu. Rev. Biochem.*, 52:467 (1983).
Lamb et al., *Proc. Natl. Acad. Sci. USA*, 77:1857 (1980).
Lu et al., *Virology*, 214:222 (1995).
Melen et al., *J. Virol.*, 81:5995 (2007).
Nayak et al., *Virus Res.*, 106:147 (2004).
Nemeroff et al., *Mol. Cell*, 1:991 (1998).
Neumann et al., *EMBO J.*, 19:6751 (2000).
Neumann et al., *Proc. Natl. Acad. Sci. USA*, 96:9345 (1999).
Noda et al., *Nature*, 439:490 (2006).
Obenauer et al., *Science*, 311:1576 (2006).
O'Neill et al., *EMBO J.*, 17:288 (1998).
Odagiri and Tobita, *Proc. Natl. Acad. Sci. USA*, 87:5988 (1990).
Odagiri et al., *J. Gen. Virol.*, 75:43 (1994).
Park and Katze, *J. Biol. Chem.*, 270:28433 (1995).
Park et al., *Proc. Natl. Acad. Sci. USA*, 96:6694 (1999).
Richardson and Akkina, *Arch. Virol.*, 116:69 (1991).
Robertson, *Rev. Med. Virol.*, 3:97 (1993).
Ruigrok and Baudin, *J. Gen. Virol.*, 76:1009 (1995).
Satterly et al., *Proc. Natl. Acad. Sci. USA*, 104:1853 (2007).
Sha and Luo, *Nat. Struct. Biol.*, 4:239 (1997).
Smith et al., *Virology*, 160:336 (1987).
Suarez and Perdue, *Virus Res.*, 54:59 (1998).
Tan and Katze, *J. Interferon Cytokine Res.*, 18:757 (1998).
Watanabe et al., *J. Virol.*, 70:241 (1996).
Yasuda et al., *Virology*, 196:249 (1993).
Ye et al., *J. Virol.*, 73:7467 (1999).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

---

What is claimed is:

1. An isolated attenuated recombinant influenza virus comprising a gene segment comprising a mutant NS2 protein gene, wherein the NS2 protein has at least one substitution that does not substantially alter the in vitro replication of the virus but is associated with attenuation of the virus in vivo, wherein the at least one substitution is a substitution for glutamate at position 74 or 75 of NS2 relative to position 74 or 75 of NS2 of influenza A virus strain WSN comprising residues in SEQ ID NO:15 which correspond to positions 67 to 82, wherein the at least one substitution is encoded by a mutation in the NS2 gene that also alters the coding region for the NS1 protein thereby yielding a NS1 protein with one or more additional amino acid residues, or wherein the substitution for glutamate is a substitution to a serine, alanine, methionine, glycine, leucine, threonine, isoleucine, or valine.

2. The virus of claim 1 further comprising a substitution for glutamate at position 67 relative to the NS2 of strain WSN.

3. The virus of claim 1 wherein the at least one substitution is at position 74.

4. The virus of claim 1 wherein the at least one substitution is at position 75.

5. The virus of claim 1 further comprising a substitution for glutamate at position 81 relative to the NS2 of strain WSN.

6. The virus of claim 1 further comprising a substitution for glutamate at position 82 relative to the NS2 of strain WSN.

7. The virus of claim 1 further comprising a substitution for tryptophan at position 78 relative to the NS2 of strain WSN.

8. The virus of claim 7 wherein the substitution for tryptophan is a substitution to serine, alanine, methionine, glycine, leucine, threonine, isoleucine, or valine.

9. The virus of claim 1 which has an additional substitution for glutamate at positions 67, 81 or 82.

10. The virus of claim 1 wherein the gene segment further comprises a mutant NS1 protein gene resulting from the mutation that yields the at least one glutamate substitution in the NS2 protein.

11. The virus of claim 1 wherein substitution for glutamate is a substitution to a serine, alanine, methionine, glycine, leucine, threonine, isoleucine, or valine.

12. The virus of claim 1 wherein the at least one substitution is encoded by a mutation in the NS2 gene that also alters the coding region for the NS1 protein thereby yielding a NS1 protein with one or more additional amino acid residues.

13. The virus of claim 1 wherein the at least one substitution is encoded by a mutation in the NS2 gene results in an amino acid substitution in the coding region for the NS1 protein.

14. A method to immunize a vertebrate comprising administering to the vertebrate an effective amount of a composition comprising the recombinant virus of claim 1.

15. An isolated attenuated recombinant influenza virus comprising a gene segment comprising a NS2 protein gene selected to encode a NS2 protein that does not have a glutamate residue at two or more positions in the M1 binding region of NS2, wherein the two or more positions correspond to positions 67, 74, 75, 81, or 82 of NS2 of influenza A virus strain WSN comprising residues in SEQ ID NO:15 which correspond to positions 67 to 82, wherein at least one of the two substitutions for glutamate is not aspartic acid.

* * * * *